US008858439B2

(12) United States Patent
Tanaka et al.

(10) Patent No.: US 8,858,439 B2

(45) Date of Patent: *Oct. 14, 2014

(54) ULTRASOUND OPERATION APPARATUS, ULTRASOUND OPERATION SYSTEM, AND CAVITATION SUPPRESSION METHOD

(75) Inventors: Kazue Tanaka, Sagamihara (JP); Yukihiko Sawada, Yoshikawa (JP); Satoshi Honma, Hino (JP)

(73) Assignee: Olympus Medical Systems Corp., Tokyo (JP)

(*) Notice: Subject to any disclaimer, the term of this patent is extended or adjusted under 35 U.S.C. 154(b) by 558 days.

This patent is subject to a terminal disclaimer.

(21) Appl. No.: 12/477,661

(22) Filed: Jun. 3, 2009

(65) Prior Publication Data

US 2010/0312111 A1 Dec. 9, 2010

(51) Int. Cl.

| | |
|---|---|
| ***A61B 8/00*** | (2006.01) |
| ***A61B 17/32*** | (2006.01) |
| ***A61B 18/14*** | (2006.01) |
| *A61B 17/22* | (2006.01) |
| *A61B 17/00* | (2006.01) |
| *A61B 18/00* | (2006.01) |

(52) U.S. Cl.

CPC .................. *A61B 17/320092* (2013.01); *A61B 2017/22009* (2013.01); *A61B 2017/22008* (2013.01); *A61B 2017/00154* (2013.01); *A61B 18/1402* (2013.01); *A61B 2018/00595* (2013.01)

USPC .......................................................... 600/439

(58) Field of Classification Search

CPC ............... A61N 7/00; A61N 7/02; A61B 8/12

USPC .................................................. 600/437, 439

See application file for complete search history.

(56) References Cited

U.S. PATENT DOCUMENTS 6,761,690 B2 7/2004 Sakurai et al.
7,714,481 B2 5/2010 Sakai (Continued)

FOREIGN PATENT DOCUMENTS

EP 1 927 321 A1 6/2008
GB 2 416 458 A 1/2006

(Continued)

OTHER PUBLICATIONS

Abstract of International PCT Publication No. WO 00/53263 A1, dated Sep. 14, 2000.

Abstract of Japanese Patent Publication No. 08-131454, dated May 28, 1996.

*Primary Examiner* — Tse Chen

*Assistant Examiner* — Hien Nguyen

(74) *Attorney, Agent, or Firm* — Scully, Scott, Murphy & Presser, P.C.

(57) ABSTRACT

An ultrasound operation apparatus includes an ultrasound transducer; a drive section that drives the ultrasound transducer using a drive signal; a probe that has a proximal end section in which the ultrasound transducer is provided and a distal end section to which ultrasound vibrations are transmitted, and that performs treatment for living tissue by using ultrasound vibrations at the distal end section; a resonance frequency tracking section that drives so as to cause ultrasound vibrations to be generated at a resonance frequency; a detection section that detects a frequency component signal of a frequency component other than a resonance frequency of the drive signal; and a cavitation suppression control section that controls so as to suppress or eliminate cavitations according to the detection result.

19 Claims, 24 Drawing Sheets

MULTIPLICATION
AMPLIFIER
VOLTAGE SIGNAL Sv
CURRENT SIGNAL Si
OSCILLATION (VCO)
PLL
CURRENT/ VOLTAGE DETECTION
DIFFERENTIAL AMPLIFIER
OUTPUT CURRENT SETTING SIGNAL
CPU
CAV SUPPRESSION CONTROL SECTION
CAVITATION LEVEL SIGNAL Sc
FILTER
CONTROL MODE SIGNAL, SETTING VALUE
SETTING SECTION
DISPLAY SECTION
FOOT SW

(56) References Cited

U.S. PATENT DOCUMENTS

| | | | | |
|---|---|---|---|---|
| 7,731,677 | B2 * | 6/2010 | Sakurai | 604/22 |
| 2001/0039389 | A1 | 11/2001 | Sakurai et al. | |
| 2002/0082528 | A1 * | 6/2002 | Friedman et al. | 601/2 |
| 2003/0056568 | A1 * | 3/2003 | Kleinberg et al. | 73/19.01 |
| 2003/0092667 | A1 * | 5/2003 | Tachibana et al. | 514/44 |
| 2003/0221561 | A1 * | 12/2003 | Milo | 96/175 |
| 2004/0078035 | A1 * | 4/2004 | Kanehira et al. | 606/28 |
| 2004/0162509 | A1 | 8/2004 | Sakurai et al. | |
| 2004/0215131 | A1 * | 10/2004 | Sakurai | 604/35 |
| 2004/0253183 | A1 * | 12/2004 | Uber et al. | 424/9.52 |
| 2005/0113690 | A1 * | 5/2005 | Halmann et al. | 600/437 |
| 2008/0316865 | A1 * | 12/2008 | Young et al. | 367/140 |
| 2010/0106019 | A1 * | 4/2010 | Friemel et al. | 600/439 |

FOREIGN PATENT DOCUMENTS

| | | |
|---|---|---|
| JP | 2001-212514 | 8/2001 |
| JP | 2001-346805 | 12/2001 |
| JP | 2002-537955 | 11/2002 |
| JP | 3754113 | 12/2005 |
| JP | 2006-130313 | 5/2006 |
| JP | 2008-055151 | 3/2008 |
| JP | 2008-506527 A | 3/2008 |
| JP | 2008-136845 | 6/2008 |
| JP | 2008-188160 | 8/2008 |
| WO | WO 2005/094701 A1 | 10/2005 |
| WO | WO 2006/008502 A2 | 1/2006 |

* cited by examiner

ULTRASOUND DRIVING APPARATUS
HIGH FREQUENCY OUTPUT APPARATUS
WATER SUPPLY/ SUCTION DEVICE
FOOT SW
FOOT SW
FOOT SW
1
2
2a
2b
2c
2d
2e
2f
2g
3
3a
3b
3c
3d
3e
3f
3g
4
4a
4b
4c
4d
4e
5
6
7
8
9
10
11
12
13
14
15
16
18

2
2a
2b
2c
2d
2e
2f
2g
5
8
14
18
19a
19b
21
22
23
24

AMPLIFIER
MULTIPLICATION
PLL
OSCILLATION (VCO)
CURRENT/ VOLTAGE DETECTION
VOLTAGE SIGNAL Sv
CURRENT SIGNAL Si
θi
θv
DIFFERENTIAL AMPLIFIER
OUTPUT CURRENT SETTING SIGNAL
FILTER
CAVITATION LEVEL SIGNAL Sc
CPU
CAV SUPPRESSION CONTROL SECTION
DISPLAY SECTION
FOOT SW
SETTING SECTION
CONTROL MODE SIGNAL, SETTING VALUE
2
2a
2b
2c
2d
2e
5
8
14
21
22
23
24
31
32
33
34
34a
35
36
37
38
39
40
40a
41
49

2
2a
2b
2c
2d
2e
14
22
34a
34
VOLTAGE SIGNAL Sv
CURRENT SIGNAL Si
CURRENT/ VOLTAGE DETECTION
35
38
FILTER
39
CAVITATION LEVEL SIGNAL Sc
5B
SWITCHING CONTROL SIGNAL
61
23
DISPLAY SECTION
AMPLIFIER
33
θi
θv
37
PLL
36
CPU
40
40a
8
FOOT SW
MULTIPLICATION
32
OSCILLATION (VCO)
31
OUTPUT CURRENT SETTING SIGNAL
CONTROL MODE SIGNAL, SETTING VALUE
24C
SETTING SECTION
DIFFERENTIAL AMPLIFIER
41
21B

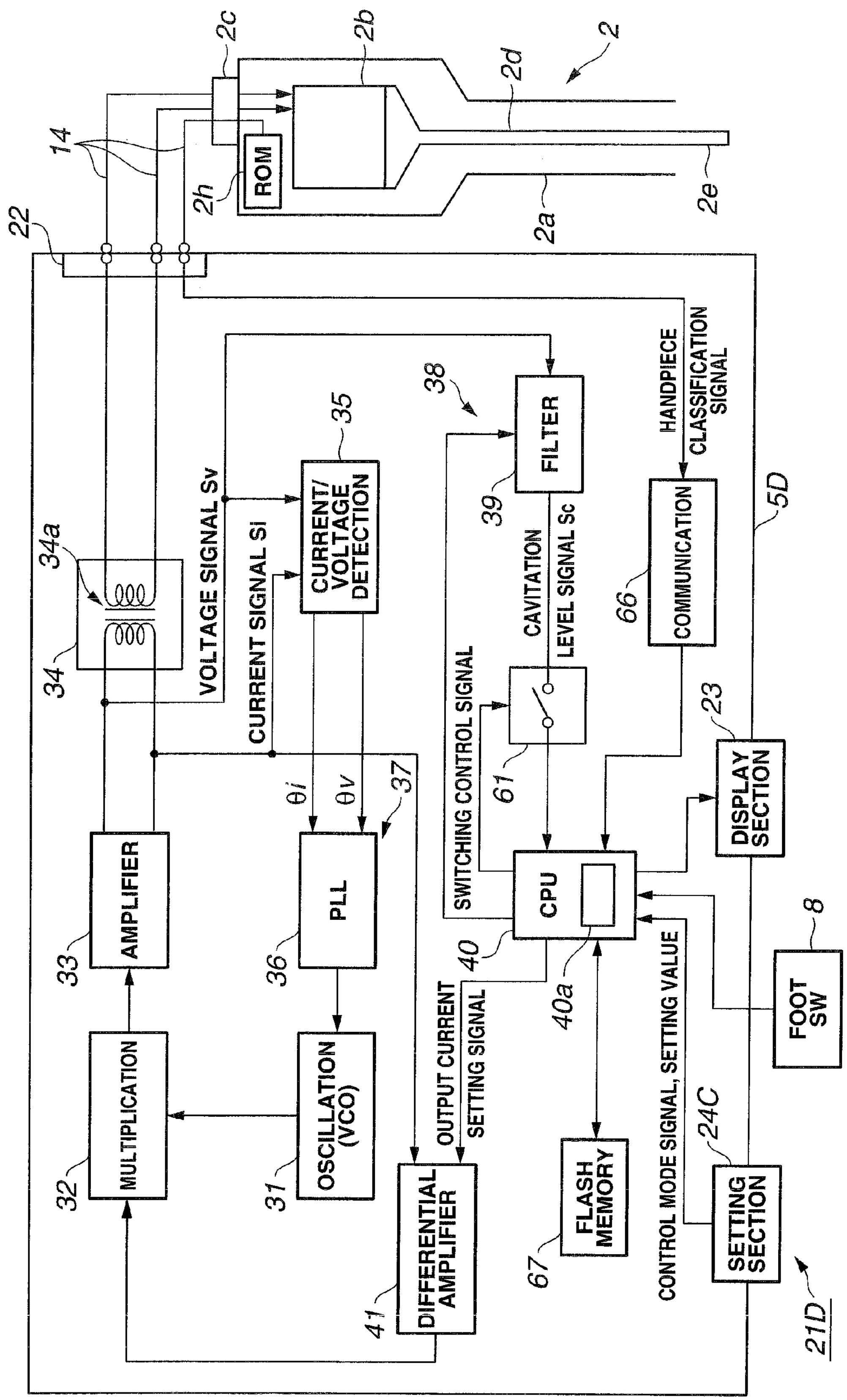
FIG.13
2
2a
2b
2c
2d
2e
2h
ROM
14
22
34
34a
VOLTAGE SIGNAL Sv
CURRENT SIGNAL Si
CURRENT/ VOLTAGE DETECTION
35
38
FILTER
39
HANDPIECE CLASSIFICATION SIGNAL
COMMUNICATION
66
CAVITATION LEVEL SIGNAL Sc
5D
SWITCHING CONTROL SIGNAL
61
23
DISPLAY SECTION
θi
θv
37
PLL
36
AMPLIFIER
33
CPU
40
40a
FOOT SW
8
OUTPUT CURRENT SETTING SIGNAL
MULTIPLICATION
32
OSCILLATION (VCO)
31
DIFFERENTIAL AMPLIFIER
41
FLASH MEMORY
67
CONTROL MODE SIGNAL, SETTING VALUE
24C
SETTING SECTION
21D

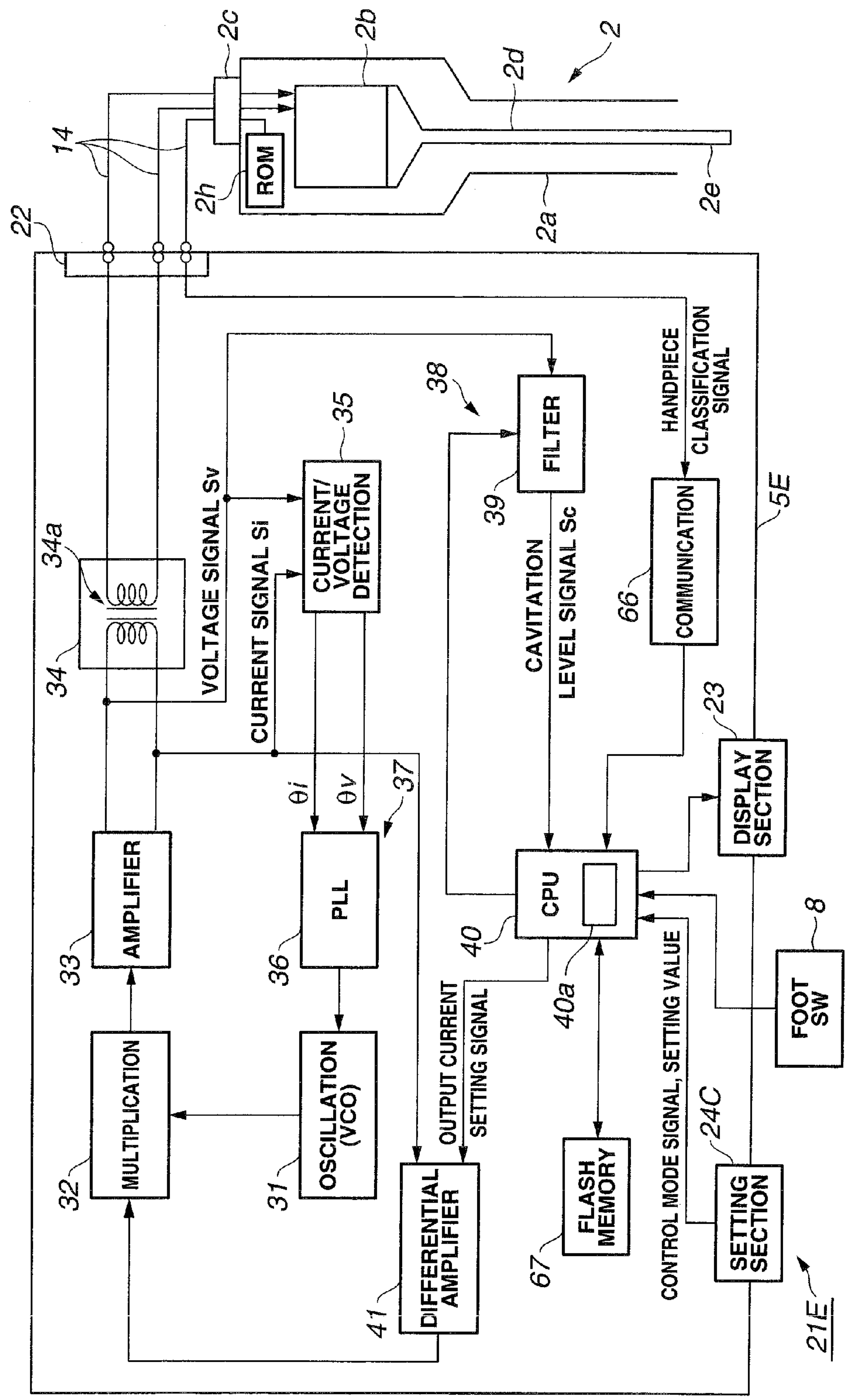
FIG.15
2
2a
2b
2c
2d
2e
2h
ROM
14
22
34
34a
VOLTAGE SIGNAL Sv
CURRENT SIGNAL Si
CURRENT/ VOLTAGE DETECTION
35
38
FILTER
39
HANDPIECE CLASSIFICATION SIGNAL
COMMUNICATION
66
5E
CAVITATION LEVEL SIGNAL Sc
AMPLIFIER
33
θi
θv
PLL
36
37
CPU
40
40a
DISPLAY SECTION
23
FOOT SW
8
MULTIPLICATION
32
OSCILLATION (VCO)
31
DIFFERENTIAL AMPLIFIER
41
OUTPUT CURRENT SETTING SIGNAL
FLASH MEMORY
67
CONTROL MODE SIGNAL, SETTING VALUE
SETTING SECTION
24C
21E 21F
2
2b
18
19b
2j
2b
19a
2c
14
22
5F
OUTPUT
CPU
34
40
FOOT SW
8

RESONANCE FREQUENCY TRACKING SECTION
Sv
Si
FILTER
DIFFERENTIAL AMPLIFIER
CPU
Sc
DISPLAY SECTION
FOOT SW
SETTING SECTION
SETTINGS STORAGE SECTION
OUTPUT CURRENT SETTING SIGNAL
WATER SUPPLY SECTION
SUCTION SECTION
WATER SUPPLY CONTROL SECTION
SUCTION CONTROL SECTION
DISPLAY SECTION
CPU
FOOT SW
SETTING SECTION
3
3a
3b
3c
3d
3e
3f
3g
1B
21H
7
14
16
12
5H
37
38
39
40
40a
41
23
24C
68
70
8
86
87
87a
88
88a
89
90
91
92
10

RESONANCE FREQUENCY TRACKING SECTION
DIFFERENTIAL AMPLIFIER
FILTER
CPU
CAV GENERATION CONTROL SECTION
DISPLAY SECTION
FOOT SW
SETTING SECTION
OUTPUT CURRENT SETTING SIGNAL
Sv
Si
Sc
2
2a
2b
2c
2d
2e
2f
2g
14
18
21J
5J
8
23
24
37
38
39
40
40a
40b
41
97

ULTRASOUND OPERATION APPARATUS, ULTRASOUND OPERATION SYSTEM, AND CAVITATION SUPPRESSION METHOD

BACKGROUND OF THE INVENTION

1. Field of the Invention

The present invention relates to an ultrasound operation apparatus that performs an operation utilizing ultrasound vibrations and also suppresses cavitations that are generated accompanying ultrasound vibrations, as well as an ultrasound operation system and a cavitation suppression method.

2. Description of the Related Art

Ultrasound operation apparatuses that perform an operation on living tissue utilizing ultrasound vibrations produced by an ultrasound transducer have been widely used in recent years. When living tissue is caused to vibrate at an ultrasound frequency, in some cases cavitations are generated since the living tissue includes liquid. A cavitation indicates that when the pressure of a liquid becomes lower than a vapor pressure that is decided by the temperature of the liquid, the liquid evaporates and vapor bubbles are produced.

Accordingly, when compression waves are generated by ultrasound vibrations, cavitations are generated accompanying the generation of negative pressure.

Therefore, for example, Japanese Patent Application Laid-Open Publication No. 2002-537955 discloses an apparatus that irradiates ultrasound for medical treatment at a location inside the body, and monitors the level of cavitations at that time using a hydrophone.

Further, International Publication No. WO2005/094701 discloses an apparatus in which a sound pressure signal receiving probe is provided in a piezoelectric element for ultrasound irradiation, and which controls ultrasound irradiation conditions by means of sound pressure signals that are discharged from cavitation bubbles by the sound pressure signal reception probe.

SUMMARY OF THE INVENTION

An ultrasound operation apparatus according to one aspect of the present invention includes:

an ultrasound transducer that is capable of generating ultrasound vibrations;

a drive section that drives the ultrasound transducer by means of a drive signal;

a probe that has a proximal end section that is operationally coupled with the ultrasound transducer, and a distal end section that generates ultrasound vibrations for treating a living tissue, the probe being used for transmitting the ultrasound vibrations generated by the ultrasound transducer from the proximal end section to the distal end section;

a resonance frequency tracking section that automatically adjusts a frequency of the drive signal so as to track a resonance frequency of the ultrasound transducer, to cause the distal end section to make ultrasound vibrations at the resonance frequency;

a detection section that detects a frequency component signal of a frequency component other than a resonance frequency of the drive signal as a cavitation detection signal; and a cavitation suppression control section that controls the drive signal so as to suppress or eliminate cavitations in accordance with a detection result from the detection section.

An ultrasound operation apparatus according to another aspect of the present invention includes:

an ultrasound transducer that is capable of generating ultrasound vibrations;

a drive section that drives the ultrasound transducer by means of a drive signal;

a probe that has a proximal end section that is operationally coupled with the ultrasound transducer, and a distal end section that generates ultrasound vibrations for treating a living tissue, the probe being used for transmitting the ultrasound vibrations generated by the ultrasound transducer from the proximal end section to the distal end section;

a resonance frequency tracking section that automatically adjusts a frequency of the drive signal so as to track a resonance frequency of the ultrasound transducer, to cause the distal end section to make ultrasound vibrations at the resonance frequency;

a detection section that detects a cavitation by detecting a frequency component signal of a frequency component other than a resonance frequency of the drive signal; and an output control section that performs control to change an output of the drive signal that drives the ultrasound transducer, in accordance with a detection result of the detection section.

An ultrasound operation system according to a further aspect of the present invention includes:

an ultrasound transducer that is capable of generating ultrasound vibrations;

a drive section that drives the ultrasound transducer;

a proximal end section that is operationally coupled with the ultrasound transducer, and a resonance frequency tracking section that tracks a resonance frequency of the ultrasound transducer for treating a tissue;

a distal end section that generates ultrasound vibrations at the tracked resonance frequency;

a probe for transmitting the ultrasound vibrations that are generated by the ultrasound transducer from the proximal end section to the distal end section;

a suction driving section that sucks a liquid in a vicinity of the distal end section;

a suction amount detection section that detects a suction amount that is sucked by the suction driving section;

a suction amount setting section that sets the suction amount;

a suction control section that controls the suction driving section in accordance with the suction amount setting section; and a cavitation suppression control section that controls the drive signal so as to suppress or eliminate cavitations in accordance with a detection result of the suction amount detection section.

A cavitation suppression method according to a further aspect of the present invention includes:

a step of applying ultrasound vibrations to a treatment portion by means of an ultrasound transducer that is capable of generating ultrasound vibrations; driving means that drives the ultrasound transducer; and a probe that has a proximal end section that is operationally coupled with the ultrasound transducer, and a distal end section that generates ultrasound vibrations for treating a tissue, the probe being used for transmitting the ultrasound vibrations generated by the ultrasound transducer from the proximal end section to the distal end section;

a resonance frequency tracking step of tracking a resonance frequency of the ultrasound transducer;

a step of detecting a signal of a frequency component other than a resonance frequency of a driving voltage or a current signal as a cavitation detection signal; and a cavitation suppression control step of controlling a drive signal that drives the ultrasound transducer so as to suppress or eliminate cavitations in accordance with a result regarding a signal that is detected in the detection step.

BRIEF DESCRIPTION OF THE DRAWINGS

FIG. 13 is a configuration diagram of an ultrasound operation apparatus according to a first modification example of the second embodiment;

FIG. 15 is a configuration diagram of an ultrasound operation apparatus according to a second modification example;

DETAILED DESCRIPTION OF THE PREFERRED EMBODIMENTS

Hereunder, embodiments of the present invention are described with reference to the drawings.

First Embodiment

Figure 1:
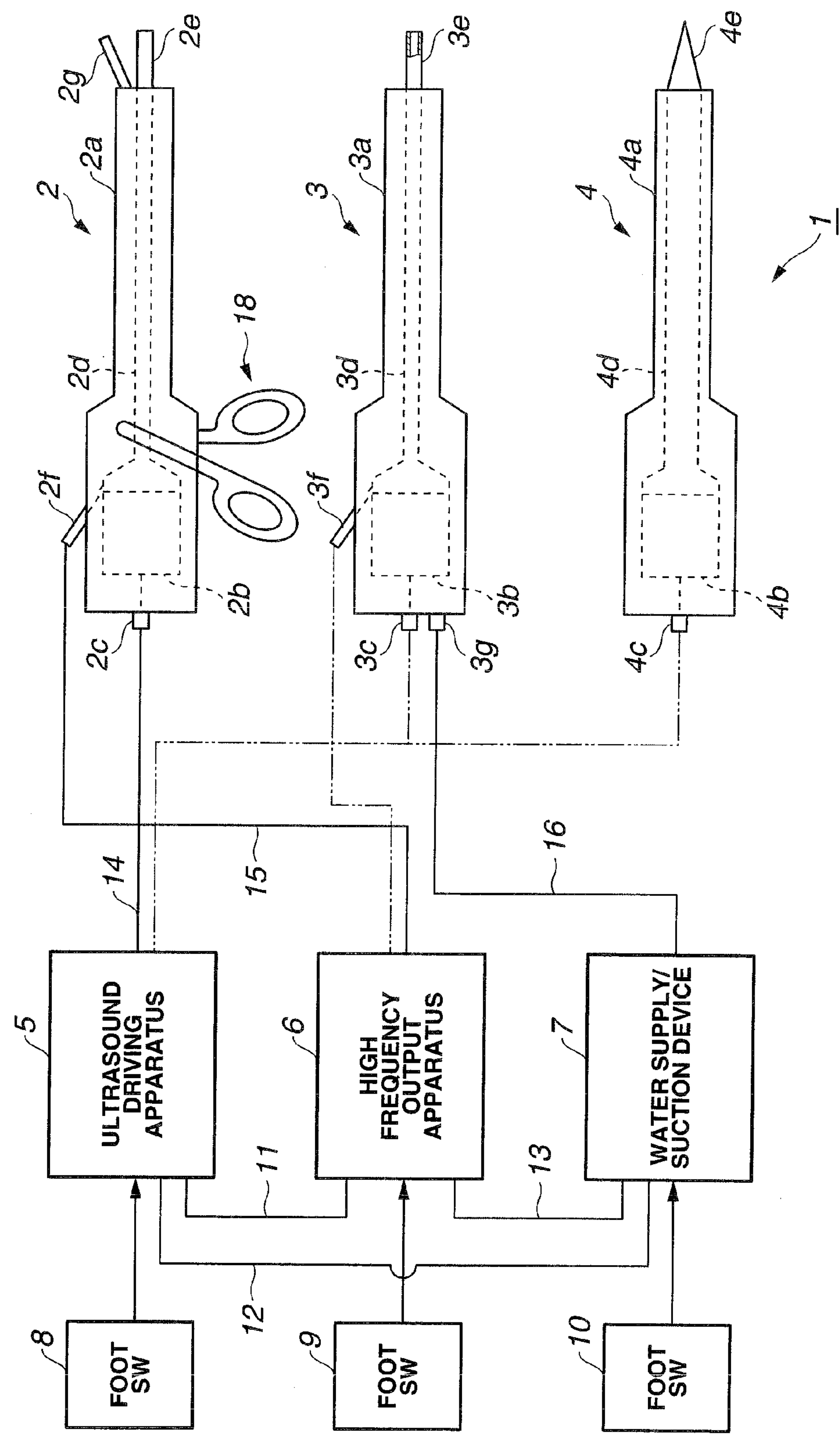
FIG. 1 is a configuration diagram that illustrates a configuration of an ultrasound operation system that includes a first embodiment of the present invention.
Figure 2:
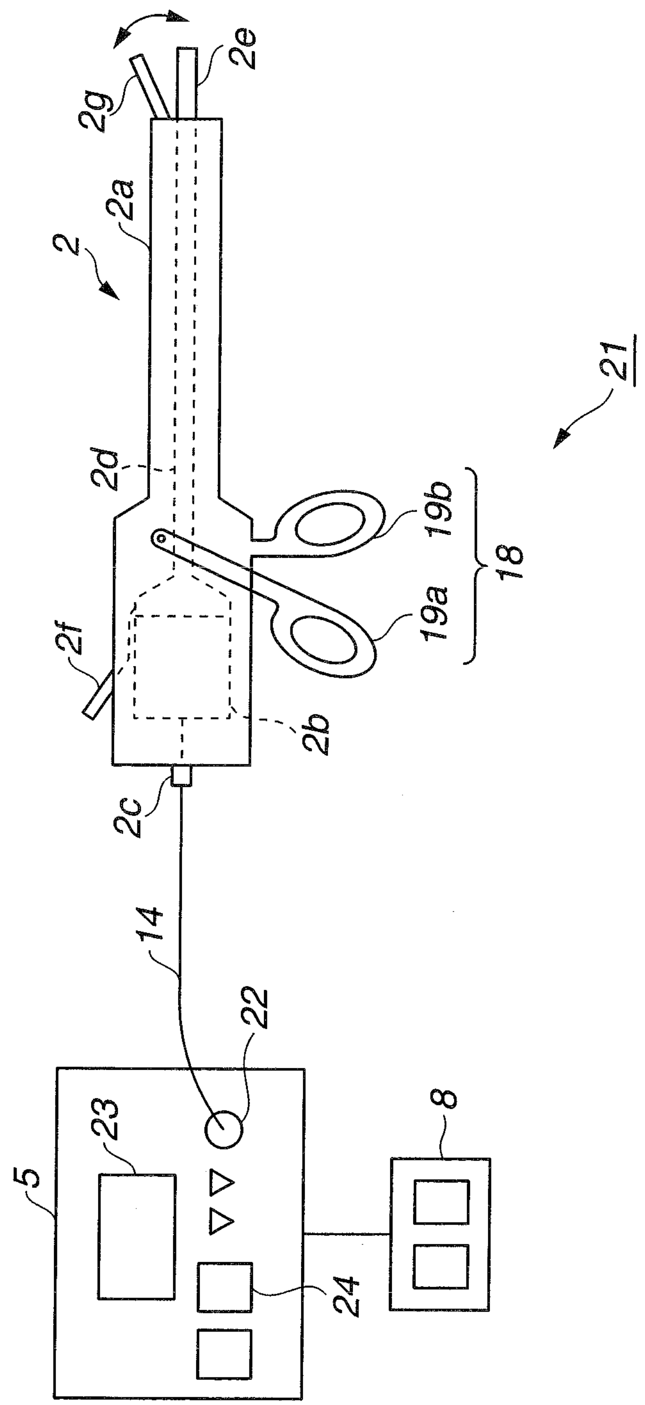
FIG. 2 is a configuration diagram of an ultrasound operation apparatus according to the first embodiment.
Figure 3:
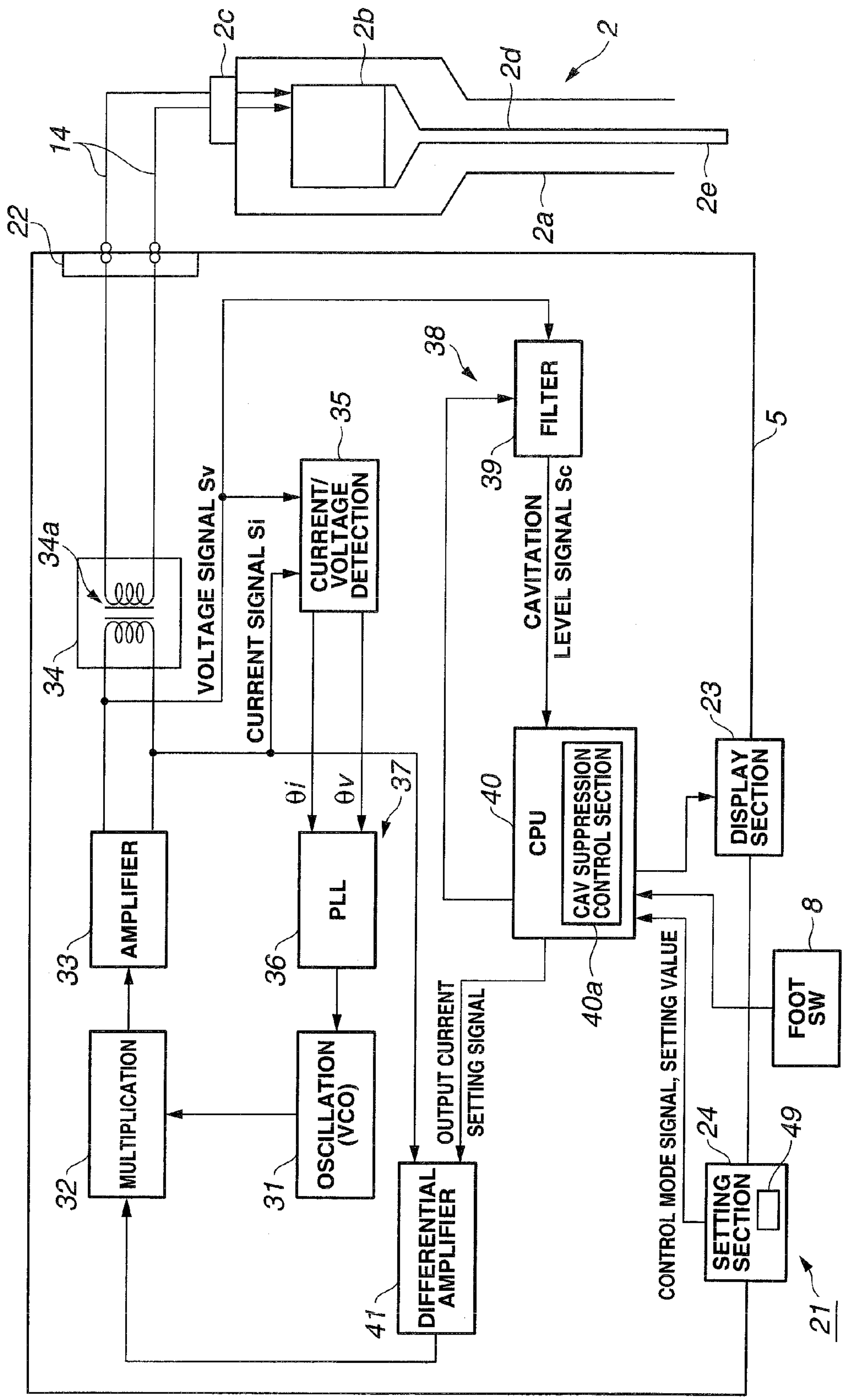
FIG. 3 is a block diagram that illustrates a configuration of an ultrasound driving apparatus in the ultrasound operation apparatus.

FIG. 1 to FIG. 7 relate to a first embodiment of the present invention. FIG. 1 illustrates a configuration of an ultrasound operation system that includes the first embodiment of the present invention. FIG. 2 illustrates a configuration of an ultrasound operation apparatus according to the first embodiment. FIG. 3 illustrates a configuration of an ultrasound driving apparatus. FIG. 4A illustrates a frequency distribution of a current signal that is detected from a drive signal at a time of cavitation generation and a time when a cavitation is not generated. In this case, although the frequency distribution of a current signal is shown, a similar distribution is obtained with a voltage signal also.

Figure 4A:
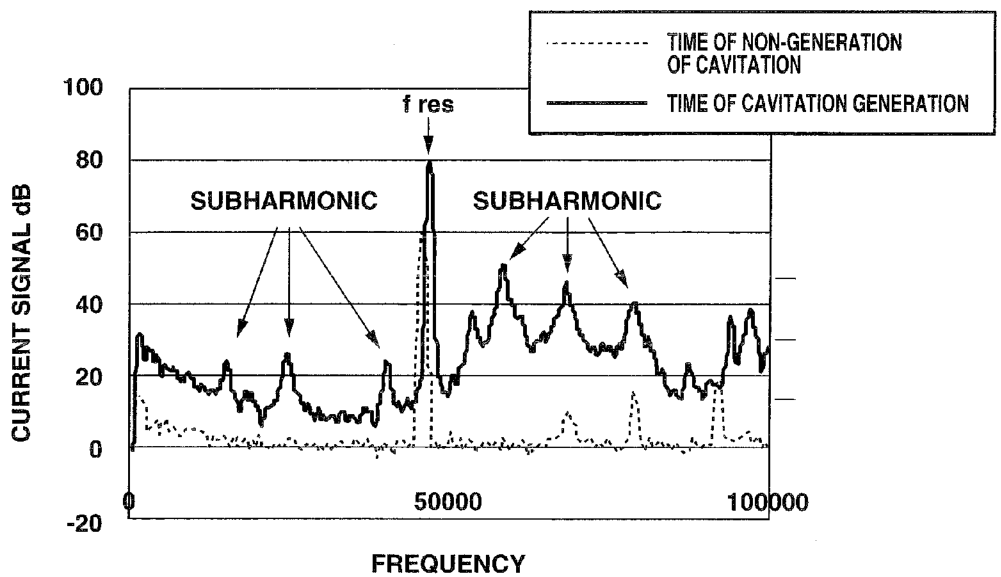
FIG. 4A is a view that illustrates a frequency distribution of a current signal that is detected from a drive signal at a time of cavitation generation and a time when a cavitation is not generated.
Figure 4B:
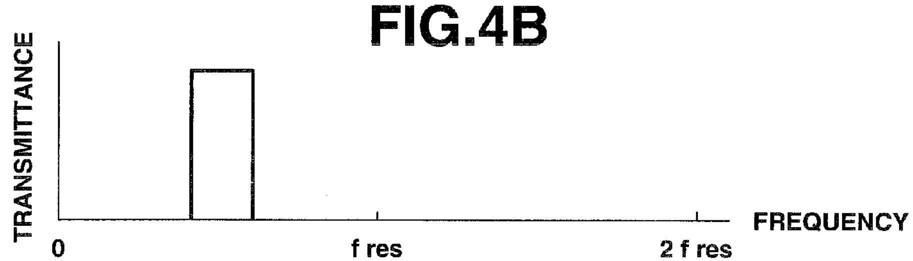
FIG. 4B to FIG. 4D are views that illustrate characteristic examples that show frequency bands that a filter circuit allows to pass therethrough.
Figure 4C:
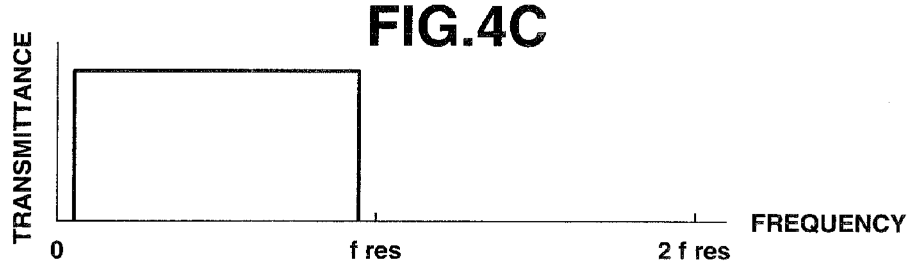
Figure 4D:
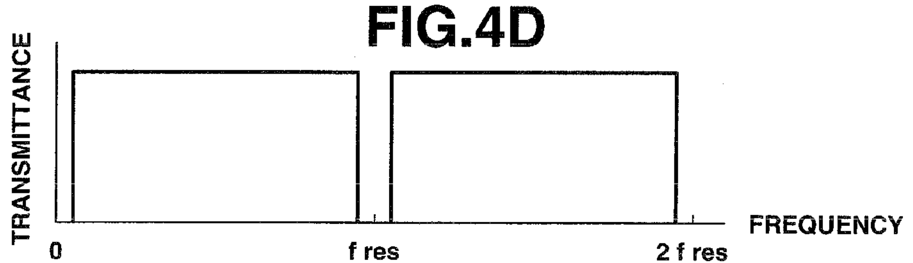
Figure 5:
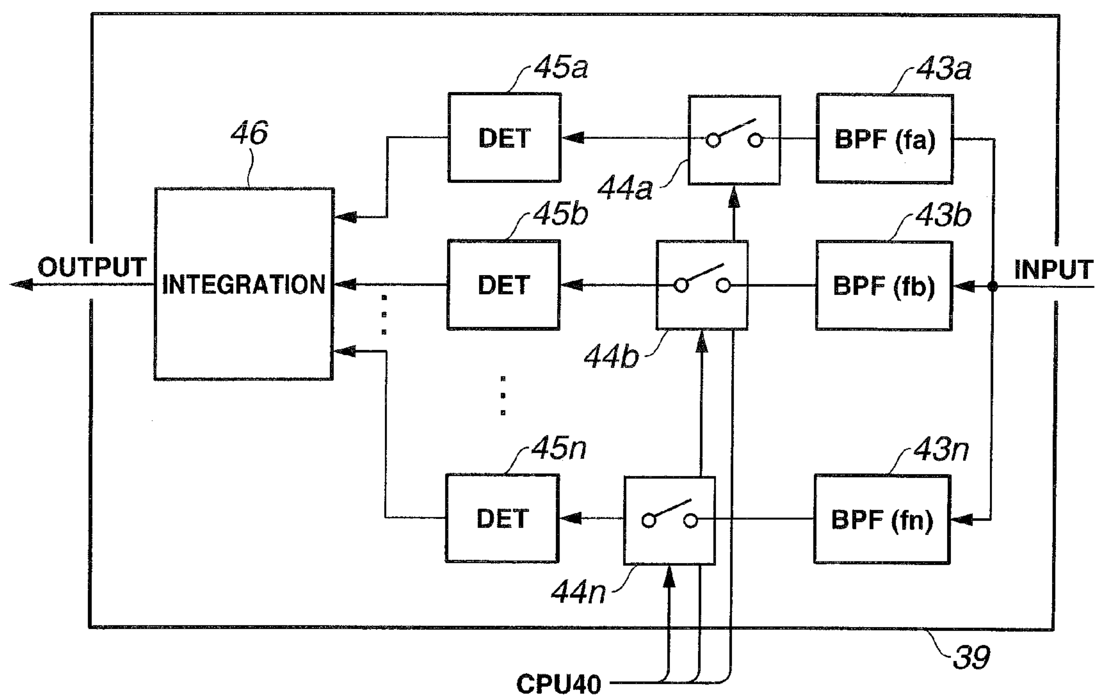
FIG. 5 is a block diagram that illustrates a configuration example of a filter circuit.
Figure 6:
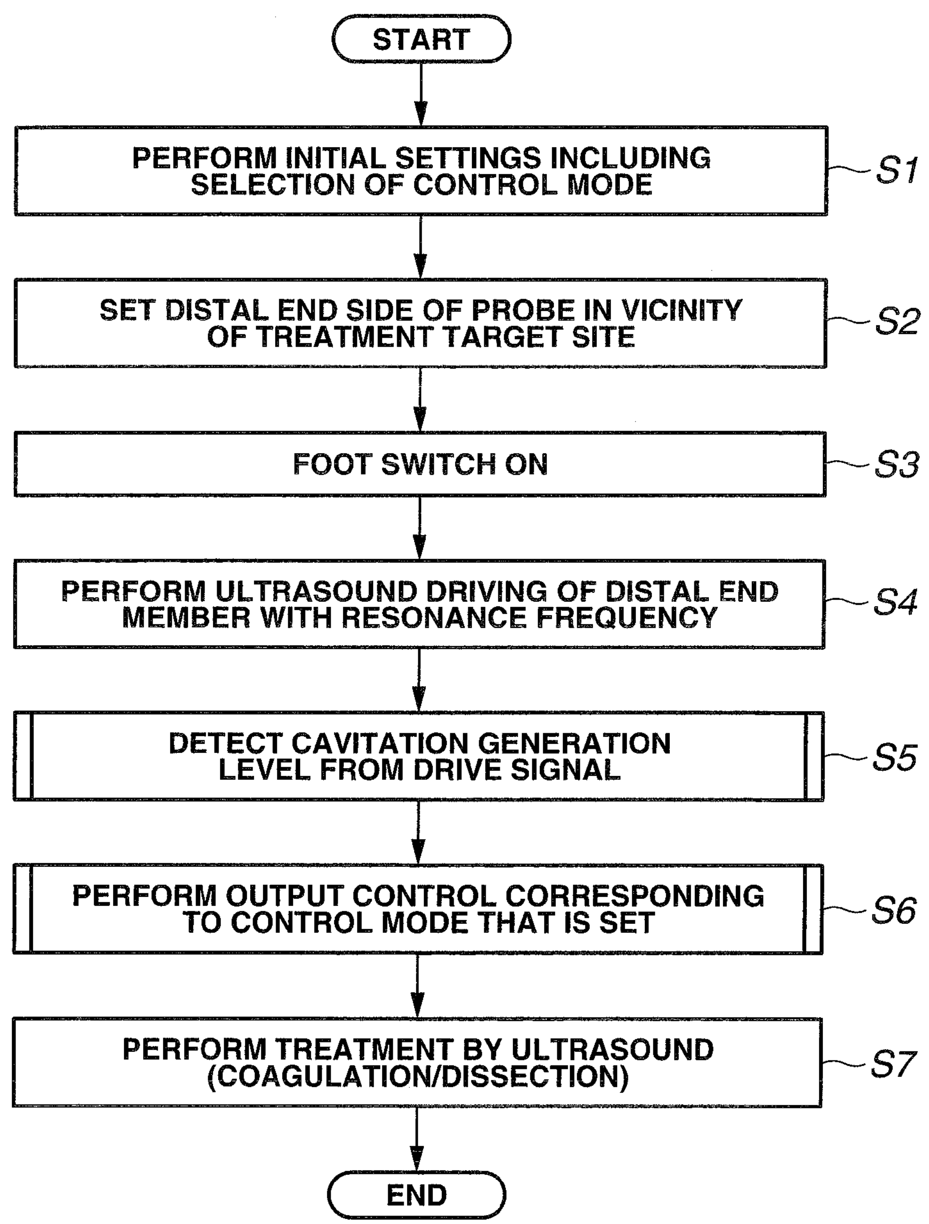
FIG. 6 is a flowchart that illustrates procedures of an ultrasound operation by an ultrasound operation apparatus.
Figure 7:
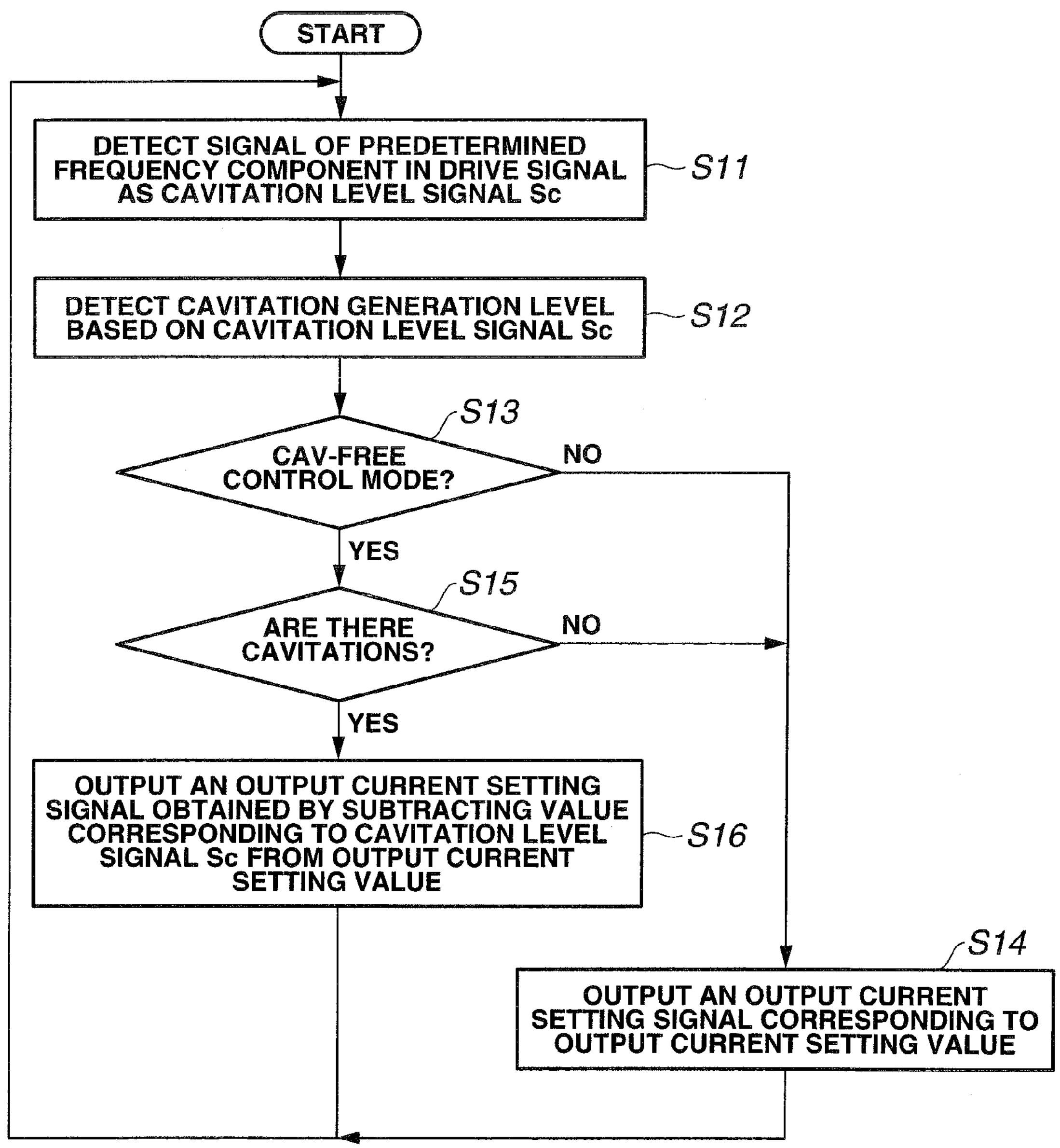
FIG. 7 is a flowchart that includes a control method of suppressing the generation of cavitations in FIG. 6.

FIG. 4B to FIG. 4D illustrate examples of filter characteristics of a filter circuit. FIG. 5 illustrates a configuration example of a filter circuit. FIG. 6 illustrates a method of treatment by an ultrasound operation apparatus. FIG. 7 illustrates a suppression method of suppressing the generation level of cavitations in FIG. 6.

As shown in FIG. 1, an ultrasound operation system 1 equipped with the first embodiment of the present invention has a first handpiece 2 as an ultrasound coagulation/dissection treatment instrument that performs a treatment such as coagulation and dissection as well as exfoliating dissection by ultrasound, a second handpiece 3 as an ultrasound/suction treatment instrument that performs a treatment such as dissection, exfoliation dissection, or crushing by ultrasound and also a suction operation, and a third handpiece 4 as an ultrasound puncture treatment instrument that performs a treatment such as puncturing by ultrasound.

Further, the ultrasound operation system 1 includes an ultrasound driving apparatus 5 that has a drive section that applies (outputs) an ultrasound drive signal to any handpiece that is actually connected among the first to third handpieces, a high frequency output apparatus 6 that applies a high frequency output signal to a handpiece that is actually connected among the first handpiece 2 and the second handpiece 3, and a water supply/suction device 7 that performs water supply and suction operations in the case of the second handpiece 3.

Foot switches 8, 9, and 10 are connected to the ultrasound driving apparatus 5, the high frequency output apparatus 6, and the water supply/suction device 7, respectively, and switch the output of the respective apparatuses "on" and "off".

The ultrasound driving apparatus 5 and the high frequency output apparatus 6 are connected by a communication cable 11 that performs communication. The ultrasound driving apparatus 5 and the water supply/suction device 7 are connected by a communication cable 12. The high frequency output apparatus 6 and the water supply/suction device 7 are connected by a communication cable 13.

Each of the handpieces I (I=2, 3, 4) among the first handpiece 2 to the third handpiece 4 includes an elongated probe 2*a*, 3*a*, and 4*a*, respectively, and also includes an ultrasound transducer (hereunder, referred to simply as "transducer") Ib capable of generating ultrasound vibrations inside a grasping section. A proximal end section of each probe Ia is disposed at the grasping section. Ultrasound vibrations generated by the transducer Ib are operationally coupled (that is, coupled so that ultrasound vibrations can be transmitted to the proximal end section) to, for example, a horn that is provided with an expanded diameter at the proximal end section of each of the probes Ia.

An ultrasound connector Ic that is electrically connected to the transducer Ib is provided at the proximal end of each handpiece I. The ultrasound connector Ic is connected to the ultrasound driving apparatus 5 via a detachable ultrasound cable 14.

When a surgeon switches the foot switch 8 "on", the ultrasound driving apparatus 5 outputs an ultrasound drive signal (hereafter, abbreviated to "drive signal") to the transducer Ib via the ultrasound cable 14. The transducer Ib generates ultrasound vibrations when the drive signal is applied thereto.

The transducer Ib transmits ultrasound vibrations to a distal end member Ie as a distal end section of the probe Ia through an ultrasound transmitting member Id inside the probe Ia, and the distal end member Ie vibrates at an ultrasound frequency.

The surgeon can perform treatment using ultrasound vibrations by, for example, grasping the grasping section on the proximal end side of a handpiece and contacting the distal end member Ie that vibrates at an ultrasound frequency against a living tissue that is a treatment target.

Further, a high frequency connector **2*f* provided on the proximal end side of the handpiece 2 or a high frequency connector 3*f* of the handpiece 3 is connected to the high frequency output apparatus 6 via a detachable high frequency cable 15. When the surgeon switches the foot switch 9 "on", the high frequency output apparatus 6 outputs a high frequency output signal to a conductor section inside the handpiece via a high frequency cable 15**. The conductor section is formed with the ultrasound transmitting member Id. Similarly to the case of ultrasound vibrations, the high frequency output signal is transmitted to the distal end member Ie of the distal end section of the probe Ia.

When the surgeon brings the distal end member Ie into contact with the living tissue, an electric current (high frequency current) of the high frequency output signal flows to the living tissue side. By means of the high frequency current, the surgeon performs high-frequency cauterization treatment with respect to the living tissue portion that is contacted.

In this case, the patient is disposed so as to contact over a wide area with a counter-electrode plate (not shown), and the high frequency current that flows through the living tissue is returned via the counter-electrode plate to the high frequency output apparatus 6 through a return cable that is connected to the counter-electrode plate.

Further, in the handpiece 3, the ultrasound transmitting member **3*d* is formed with a conduit, and a hollow section of the conduit serves as a suction passage (water supply is performed between the conduit of the ultrasound transmitting member 3*d* and an outer sheath (not shown)). The distal end member 3*e*** that serves as the distal end of the conduit is open.

A water supply/suction connector **3*g* is provided on the proximal end side of the handpiece 3. A water supply/suction tube 16 that is detachably connected to the handpiece 3 is connected to the water supply/suction device 7**.

The water supply/suction tube 16, for example, branches into a water supply conduit and a suction conduit inside the water supply/suction device 7, and the water supply conduit connects to a water supply apparatus and the suction conduit connects to a suction apparatus.

When the surgeon performs an operation to switch "on" a water supply switch of the foot switch 10, a water supply pump that is included in the water supply apparatus is activated and feeds water. The fed water passes through a hollow section forming the ultrasound transmitting member **3*d* and is ejected from an opening of the distal end member 3*e***.

Further, when the surgeon performs an operation to switch "on" a suction switch of the foot switch 10, a suction pump that is included in the suction apparatus is activated and performs a suction action. Thereupon, tissue pieces and the like that are produced at the time of treatment (crushing with ultrasound vibrations) are sucked from the opening of the distal end member **3*e*** and discharged to the suction apparatus.

Although FIG. 1 shows a configuration example for a case of performing treatment by also using a function other than ultrasound vibrations, as shown in FIG. 2, an ultrasound operation apparatus 21 may also be configured that performs treatment utilizing only ultrasound vibrations.

The ultrasound operation apparatus 21 shown in FIG. 2 includes, for example, the handpiece 2 that performs coagulation/dissection treatment by ultrasound vibrations, an ultrasound driving apparatus 5 that outputs a drive signal to the handpiece 2, and a foot switch 8 that is connected to the ultrasound driving apparatus 5 and switches the output of a drive signal "on" and "off". The handpiece 2 is connected to a connector 22 of the ultrasound driving apparatus 5 via an ultrasound cable 14.

In this connection, instead of the handpiece 2, the handpiece 3 or the handpiece 4 may be connected to the ultrasound driving apparatus 5. Further, as described in an embodiment mentioned below, a configuration may also be adopted in which treatment is performed in combination with use of the high frequency output apparatus 6.

As shown in FIG. 2, the handpiece 2 is provided with a handle 18 on the proximal end side thereof. The surgeon grasps the handle 18 and performs an opening/closing operation.

In the handle 18, the upper end side of a moveable handle **19*a*** is rotatably supported at a pivot section.

By performing an opening/closing operation that closes the moveable handle **19*a* to a fixed handle 19*b* side or opens the moveable handle 19*a* to a side away from the fixed handle 19*b*, a moveable distal end member 2*g* that is rotatably supported adjacent to the distal end member 2*e* can be opened/closed with respect to the distal end member 2*e* through an unshown wire that is passed through the inside of the probe 2*a***.

Thus, the handpiece 2 can be opened and closed so as to grasp living tissue by means of the distal end member **2*e* as a fixed distal end member and the moveable distal end member 2*g***.

More specifically, by applying ultrasound vibrations to living tissue in a state in which the living tissue is grasped by the distal end members **2*e* and 2*g*, the handpiece 2 can generate frictional heat in the living tissue and perform coagulation or dissection treatment of the living tissue that is grasped. It is also possible to set the handpiece 2 in an open state in which the distal end side is opened, and perform treatment such as crushing by means of the protruding distal end member 2*e***.

When performing treatment in a state in which the living tissue is grasped, there are normally many cases in which the surgeon desires to perform treatment with suppressing the generation of cavitations.

On a front panel of the ultrasound driving apparatus 5 are provided a display section 23 that shows a display, and a setting section 24 that sets a setting value of a signal to be outputted as an ultrasound drive signal and the like.

FIG. 3 illustrates a configuration of the ultrasound driving apparatus 5 that is included in the ultrasound operation apparatus 21 according to the present embodiment. In this connection, FIG. 3 shows the fundamental component parts of the handpiece 2 (the situation is substantially the same for the handpieces 3 and 4) that is connected to the ultrasound driving apparatus 5. Hereunder, although a description is given for a case in which I=2 as the handpiece I, the following description can also be applied to cases in which I=3 or I=4, excluding a structure that is unique to the handpiece 2.

The ultrasound driving apparatus 5 has an oscillating circuit 31, a multiplier 32 into which an oscillation signal that is generated by the oscillating circuit 31 is inputted from one input end, an amplifier 33 that amplifies a signal that is multiplied by the multiplier 32, and an output circuit 34 that isolates and outputs a drive signal that is amplified by the amplifier 33.

The output circuit 34 includes, for example, a transformer 34*a*. A drive signal that is amplified at the amplifier 33 is inputted to a primary winding of the transformer 34*a*. A drive signal that is isolated from the drive signal on the primary winding is outputted from a secondary winding that is electromagnetically coupled with the primary winding. In this connection, the primary winding side of the transformer 34*a* forms a secondary circuit, and the secondary winding side thereof forms a patient circuit A connector 22 of an output terminal from which a drive signal is outputted on the patient circuit side is connected via detachably connected ultrasound cables 14 with a transducer 2*b* that is contained inside the handpiece 2 that vibrates at an ultrasound frequency.

Further, the primary winding of the transformer 34*a* is connected with a current/voltage detecting circuit 35 that detects a current of a drive signal flowing to the primary winding and a voltage at both ends thereof, and also detects a phase of the current and a phase of the voltage.

A current phase signal θi and a voltage phase signal θv detected by the current/voltage detecting circuit 35 are outputted to a PLL (phase-locked loop) circuit 36.

The PLL circuit 36 applies a control signal to the oscillating circuit 31. In the control signal, the signal level that is outputted changes in accordance with a phase difference between the current phase signal θi and the voltage phase signal θv that are inputted to the PLL circuit 36. At the oscillating circuit 31, an oscillation frequency changes with a signal level that is applied to a control inputted end. That is, the oscillating circuit 31 is formed, for example, by a voltage-controlled oscillator (VCO).

The PLL circuit 36 applies a control signal that controls so as to reduce the phase difference between the current phase signal θi and the voltage phase signal θv, more specifically, an oscillation frequency adjusting signal that is described below, to the control input end of the oscillating circuit 31. Accordingly, at the oscillating circuit 31, by means of a closed loop using the PLL circuit 36, the oscillation frequency is automatically adjusted so that a phase difference between the current phase signal θi and the voltage phase signal θv becomes 0.

A state in which the phase difference between the current phase signal θi and the voltage phase signal θv becomes 0 is a drive frequency that corresponds to a resonance frequency of the transducer 2*b*. Therefore, the PLL circuit 36 automatically adjusts (controls) the oscillation frequency so as to drive the transducer 2*b* with a drive signal at the resonance frequency of the transducer 2*b*.

In other words, when driving the transducer 2*b* with a drive signal, the closed-loop circuit system between the oscillating circuit 31 and the PLL circuit 36 forms a resonance frequency tracking section 37 that automatically adjusts the frequency of the drive signal so as to track the resonance frequency of the transducer 2*b*. The resonance frequency tracking section 37 constitutes a drive section that outputs a drive signal at the resonance frequency.

The present embodiment is also provided with a detection section 38 that, as described below, detects a cavitation that is generated with the distal end member 2*e* of the probe 2*a* (to which ultrasound vibrations of the transducer 2*b* are transmitted) based on a drive signal of the primary winding side of the aforementioned output circuit 34 from a drive signal as a physical quantity that changes as a result of the cavitation.

For example, a voltage signal Sv as a physical quantity that changes as a result of a cavitation in a drive signal is inputted into a filter circuit 39 that has frequency transmission characteristics (filter characteristics) for extracting a predetermined frequency component. In this connection, as mentioned later, the current in the drive signal is controlled so as to become a constant current with a predetermined time constant. Therefore, detecting a voltage value (that passed through the filter circuit 39) in the voltage signal Sv is approximately equivalent to detecting an impedance value.

In this connection, in addition to detecting a voltage value or an impedance value as the aforementioned physical quantity, the detection section 38 may also be configured to detect a current value of a current signal. In this case, for example, a configuration may be adopted so as to perform detection in a state in which the voltage signal Sv is controlled so as to become a constant voltage with a predetermined time constant.

The filter circuit 39 has characteristics such that a predetermined frequency component other than at least a resonance frequency (i.e. drive frequency) of the transducer 2*b* that is driven by the drive signal passes therethrough.

A voltage signal as a frequency component signal of a predetermined frequency component that is outputted from the filter circuit 39 becomes a detection signal that corresponds to the generation level of cavitations that are generated with the transducer 2*b*, i.e. a cavitation level signal Sc.

The aforementioned detection section 38 is constituted using the filter circuit 39 that generates the cavitation level signal Sc. In this connection, the detection section 38 can also be regarded as having a configuration that includes the CPU 40 that determines the existence/non-existence of a cavitation based on the cavitation level signal Sc, and determines the level of cavitation generation.

The cavitation level signal Sc that is outputted from the filter circuit 39 is inputted to a central processing unit (CPU) 40 as a control section that performs control of each section of the ultrasound driving apparatus 5.

Further, the CPU 40 variably controls an output value of a drive signal that determines the amplitude of ultrasound vibrations at the distal end member 2*e* of the probe 2*a* based on the physical quantity that is detected by the detection section 38.

The CPU 40 determines the cavitation generation level based on the level of the cavitation level signal Sc that is inputted, and also has a function of a cavitation suppression control section (abbreviated to "CAV suppression control section" in FIG. 3) 40*a* that suppresses generation of cavitations.

FIG. 4A is a view that shows the frequency spectrum distribution of the voltage signal Sv when a cavitation is not generated (time of non-generation of cavitations) and when a cavitation is generated (time of cavitation generation) by the transducer 2*b* that is driven by a drive signal of the ultrasound driving apparatus 5. In this connection, in FIG. 4A a resonance frequency f res is 47 kHz.

Irrespective of the existence/non-existence of cavitation generation, the voltage signal Sv has a highest peak at the resonance frequency f res (47 kHz). When a cavitation is not generated, the voltage signal Sv does not have a prominent peak at a frequency other than the resonance frequency f res.

In contrast, when a cavitation is generated, at frequencies other than the resonance frequency f res, the level of the voltage signal Sv is higher than a time when a cavitation is not generated.

More specifically, at a time when a cavitation is generated, the level of subharmonics as frequencies of divisors such as ½ or ¼ of the resonance frequency f res or of differences of these divisors becomes considerably higher than at a time when a cavitation is not generated, and the level of a frequency component other than a subharmonic also becomes higher than when a cavitation is not generated.

Therefore, a cavitation generation level can be detected by detecting signal levels for the voltage signal Sv as described above, excluding levels in the vicinity of the resonance frequency f res thereof.

The cavitation level signal Sc as an output signal of the filter circuit 39 is inputted to the CPU 40 that has a function of an output control section that controls driving of the transducer 2*b* (in other words, ultrasound vibrations of the distal end member 2*e*). The output control section includes the function of the aforementioned cavitation suppression control section 40*a*.

An output current setting value that is set by the surgeon from the setting section 24 is inputted to the CPU 40.

The setting section 24 is also provided with, for example, a switching button 49 that switches between a case in which the apparatus is operated in a constant current control mode as a first control mode and a case in which the apparatus is operated in a constant current control mode in a state in which generation of cavitations is suppressed (hereunder, referred to as "cavitation-free control mode") as a second control mode.

In other words, the setting section 24 has setting means that performs output control in a cavitation-free control mode as a control mode that suppresses or eliminates the generation of cavitations.

The setting section 24 outputs an output current setting value (abbreviated as "setting value" in FIG. 3) and a control mode signal from the switching button 49 to the CPU 40.

According to the present embodiment, in the constant current control mode as the first control mode, the CPU 40 performs output control of the drive signal so as to maintain an output current value that is set by the setting section 24 irrespective of the existence or non-existence of cavitation generation.

In contrast, in the cavitation-free control mode as the second control mode, the CPU 40 suppresses the generation of cavitations using the function of the cavitation suppression control section 40*a*, and thereafter the CPU 40 performs output control of the drive signal so as to maintain an output current value that is set by the setting section 24.

In the case of the constant current control mode, the CPU 40 outputs an output current setting signal that corresponds to an output current setting value from the setting section 24 to the differential amplifier 41.

In contrast, in the case of the cavitation-free control mode, the CPU 40 outputs an output current setting signal obtained by subtracting a value corresponding to the cavitation level signal Sc from the output current setting value from the setting section 24 to the differential amplifier 41.

A current signal Si in the drive signal is also inputted into the differential amplifier 41. In this connection, although the current signal Si is actually detected by, for example, a current sensor or the like that detects the current of a drive signal that is provided inside the current/voltage detecting circuit 35, in FIG. 3 the current signal Si that is detected is illustrated in a simplified form.

The differential amplifier 41 outputs to the multiplier 32 a signal of a differential value that is obtained by subtracting the current signal Si from the output current setting signal.

The multiplier 32 multiplies a value of another input end side into which is inputted a signal from the differential amplifier 41 by the oscillation signal from the oscillating circuit 31, and outputs the result to the amplifier 33. In this case, the value of the other input end side is a value obtained by adding the output signal of the differential amplifier 41 (subtracting when the output signal of the differential amplifier 41 is negative) to a standard value 1.

Accordingly, the current signal Si in the drive signal is controlled by a closed loop system so that a value of an output current setting signal that is outputted from the CPU 40 is maintained as an averaged constant current value. In this manner, the output value of a drive signal supplied to the transducer 2*b* is controlled.

For example, in the case of the cavitation-free control mode, when the cavitation level signal Sc is generated as described above, the value of the output current setting signal that is outputted from the CPU 40 is reduced by the level quantity thereof, and constant current control is performed by a closed loop.

Therefore, constant current control is performed so as to maintain a state in which the cavitation level signal Sc ceases to exist.

In this connection, a time constant of a control system based on the current signal Si of the drive signal is, for example, around 8 ms, and the current signal Si changes within the range of this time constant.

An operation signal that switches output of a drive signal from the foot switch 8 "on" or "off" is inputted to the CPU 40, and control is performed to switch output of the drive signal "on" or "off" in accordance with the operation signal.

Further, the CPU 40 is connected with the display section 23 provided on the front panel or the like, and an ultrasound output value or the like is displayed on the display section 23.

FIG. 4B and FIG. 4C illustrate an example of the filter characteristics of the filter circuit 39, and FIG. 5 shows a configuration example thereof.

FIG. 4B illustrates a case in which characteristics are set that allow a frequency band of one portion of a low frequency side to pass through. More specifically, FIG. 4B illustrates a case in which characteristics are set that allow a frequency band including a subharmonic (divisor) of ½ of the resonance frequency f res to pass through.

FIG. 4C illustrates a case in which characteristics are set to a band that allows frequencies from around 5% of the resonance frequency f res to a frequency that is 5% lower than the resonance frequency f res (i.e. a frequency equal to 95% of the resonance frequency f res) to pass through.

FIG. 4D illustrates a case in which, in addition to the band characteristics shown in FIG. 4C, band characteristics are set that allow frequencies from around 5% higher than the resonance frequency f res to a frequency that is 5% lower than a frequency (2 f res) of a second-order harmonic wave of the resonance frequency f res to pass through.

The filter circuit 39 shown in FIG. 5 includes, for example, a plurality of bandpass filters (abbreviated as "BPF" in FIG. 5) 43*a*, 43*b*, . . . , 43*n*; switches 44*a*, 44*b*, . . . , 44*n*; wave detectors 45*a*, 45*b*, . . . , 45*n*; and an integrator 46.

In this connection, a passing frequency band of the bandpass filters 43*a*, 43*b*, . . . , 43*n* is denoted in abbreviated form as fa, fb, . . . , and fn. The relationship between the passing frequency bands in this case is, for example, fa<fb< . . . <fn.

A selection can be made to switch the switches 44*a*, 44*b*, . . . , 44*n* "on" or "off", for example, by making a setting from the setting section 24 via the CPU 40. In this case, a configuration may also be adopted that enables a direct selection from the setting section 24.

By selecting whether to switch the switches 44*a*, 44*b*, . . . , 44*n* "on" or "off", an arbitrary passing frequency band can be set. After frequency components that have passed through the switches 44*a*, 44*b*, . . . , 44*n* that have been switched "on" are detected by the wave detectors 45*a*, 45*b*, . . . , 45*n*, the frequency components are integrated at the integrator 46.

The integrated signal obtained by integration at the integrator 46 is outputted to the CPU 40 as the cavitation level signal Sc. An accumulator may be used instead of the integrator 46.

A configuration may also be adopted in which, instead of integrating at the filter circuit 39, integration is performed on the CPU 40 side.

Operations in the ultrasound driving apparatus 5 configured in this manner will now be described referring to FIG. 6. FIG. 6 is a view that shows procedures of an ultrasound operation that includes cavitation suppression control according to the ultrasound driving apparatus 5.

For example, as shown in FIG. 2, the surgeon connects a handpiece (in FIG. 2, the handpiece 2 that is mainly for performing coagulation/dissection) to be used in the treatment to the ultrasound driving apparatus 5 via an ultrasound cable.

Further, as shown in step S1, the surgeon performs initial settings such as setting the current setting value and the control mode using the setting section 24 in accordance with the living tissue to be treated (i.e. the site to be treated).

Subsequently, using an unshown trocar, the surgeon inserts an endoscope and the probe 2*a* of the handpiece 2 into the abdomen or the like of the patient. The surgeon then sets the distal end side of the probe 2*a* in the vicinity of the treatment target site inside the body under observation using the endoscope, as shown in step S2.

Next, in step S3, the surgeon switches the foot switch 8 "on" to start treatment by ultrasound. A drive signal is applied to the transducer 2*b* of the handpiece 2 from the ultrasound driving apparatus 5, and the transducer 2*b* vibrates at an ultrasound frequency.

The ultrasound vibrations are transmitted to the distal end member 2*e* on the distal end side of the probe 2*a*, and as shown in step S4, the distal end member 2*e* makes ultrasound vibrations at the resonance frequency f res of the transducer 2*b*.

In this case, the ultrasound driving apparatus 5 controls so as to track a state in which the transducer 2*b* is driven with the resonance frequency f res thereof by means of the resonance frequency tracking section 37 using the PLL circuit 36. Accordingly, the transducer 2*b* makes ultrasound vibrations at the resonance frequency f res, and further, the distal end member 2*e* of the distal end section also makes ultrasound vibrations at the resonance frequency f res.

Further, in this case, when a cavitation is generated by ultrasound vibrations of the distal end member 2*e*, the distal end member 2*e* receives a force produced by breaking of small bubbles caused by generation of the cavitation, and that force affects the ultrasound vibrations of the transducer 2*b* from the distal end member 2*e*. Subsequently, as shown in FIG. 4A, a frequency component produced by the cavitation is superimposed on the original drive signal. As described above, the frequency spectrum of the original drive signal enters a state of having a distorted frequency spectrum due to generation of the cavitation.

Subsequently, as shown in step S5, the CPU 40 detects the cavitation generation level from the cavitation level signal Sc that is detected by the filter circuit 39 from the drive signal.

Next, in step S6, the CPU 40 controls output of the drive signal corresponding to the control mode that is previously set by the setting section 24 in accordance with the detected cavitation generation level. More specifically, the CPU 40 performs output control of a drive signal that corresponds to the normal constant current control mode or the cavitation-free control mode.

Under this control, as shown in step S7, the surgeon performs treatment such as coagulation and dissection by means of ultrasound vibrations.

FIG. 7 is a view that illustrates operations to detect the cavitation level and to perform control corresponding to the control mode that is previously set in accordance with the detection result according to steps S5 and S6 shown in FIG. 6. In step S11, the filter circuit 39 outputs a predetermined frequency component excluding the frequency of a drive signal as the cavitation level signal Sc.

As shown in step S12, the CPU 40 detects the cavitation generation level from the cavitation level signal Sc.

As shown in step S13, the CPU 40 determines whether or not the control mode is, for example, the cavitation-free control mode (abbreviated to "CAV-free control mode" in FIG. 7).

When the control mode is not the cavitation-free control mode, as shown in step S14, the CPU 40 performs output control so as to maintain the output current setting value that is set by the setting section 24. More specifically, the CPU 40 outputs an output current setting signal corresponding to the output current setting value to the differential amplifier 41. The CPU 40 then returns to the processing of step S11.

By means of this output control, the output value of the drive signal operates in correspondence with the normal constant current control mode.

In contrast, when it is determined in step S13 that the control mode is the cavitation-free control mode, the CPU 40 performs output control to suppress (eliminate) cavitations by means of steps S15 and S16.

In step S15, the CPU 40 determines whether or not cavitations exist based on the existence/non-existence of the cavitation level signal Sc. When there are cavitations, as shown in step S16, the CPU 40 outputs to the differential amplifier 41 an output current setting signal corresponding to a subtraction value obtained by subtracting an amount corresponding to the level of the cavitation level signal Sc from the output current setting value. The CPU 40 then returns to the processing of step S11.

By means of this output control, since the output value of the drive signal is controlled so as to decrease in accordance with the level of cavitations when cavitations are being generated, a state is quickly entered that maintains the output value in a state in which cavitations are not generated.

In this connection, in step S15, if cavitations are not being generated, the routine moves to step S14. In this case, the state is one in which cavitations are not being generated, and the CPU 40 performs output control so as to maintain the output current setting value that is set by the setting section 24.

According to the present embodiment that performs treatment with respect to a living tissue that is a treatment target by the above described control, the existence/non-existence of cavitation generation and the cavitation generation level can be precisely detected with a simple configuration.

That is, according to the present embodiment, a cavitation generation level and the like can be precisely detected from a voltage signal or the like of a frequency component excluding the drive frequency or the resonance frequency f res based on the filter circuit 39 in a drive signal that drives the transducer 2*b*.

Furthermore, since the present embodiment controls so as to decrease output of the drive signal in accordance with a detected level of cavitations, the generation of cavitations can be rapidly eliminated.

According to the present embodiment, a surgeon can select to perform treatment for medical care in a cavitation-free state.

In this connection, a surgeon can also perform treatment in a mode which controls output of a drive signal with a constant current control mode, irrespective of the existence/non-existence of cavitations.

As described above, according to the present embodiment, with a simple configuration it is possible to precisely detect the generation of cavitations and a generation level from a voltage signal or the like of a frequency component excluding the drive frequency and frequency components in the vicinity of the resonance frequency f res based on the filter circuit 39 in a drive signal that drives the transducer 2*b*.

In this connection, Japanese Patent Application Laid-Open Publication No. 2008-188160 as an example of the related art discloses an ultrasound operation apparatus that has a drive circuit that drives a handpiece at a frequency and amplitude that correspond to an alternating current. The ultrasound operation apparatus includes a cavitation suppression circuit that has conversion means that converts an output end voltage of the drive circuit into a direct current voltage, comparison means that compares the direct current voltage from the conversion means with a predetermined threshold value, and voltage control means that, in a case in which the comparison result from the comparison means exceeds the threshold value, lowers the voltage value of the alternating current.

According to this example of the related art, it is described that practical application is made of the fact that when a load state of a piezo element included in a vibration generation section is changed by generation of a cavitation, although an alternating voltage value output by an output circuit (provided with a drive circuit) changes very little, the outputted voltage value fluctuates in proportion to the load state.

In contrast to the related art example, the present embodiment is configured so as to detect a cavitation using at least a voltage value, an impedance value, and a current value of a frequency component excluding the vicinity of a frequency used for driving in a drive signal.

Accordingly, the present embodiment is capable of adequately decreasing the influence of a drive signal to detect the existence/non-existence of cavitation generation and the generation level with a high accuracy.

That is, according to the present embodiment, by detecting frequency components excluding the vicinity of the frequency of a drive signal, it is possible to detect, for example, a cavitation generation level based on the level of a cavitation level signal Sc, without receiving virtually any influence by the output level of the drive signal.

In this case, the existence/non-existence of cavitation generation can be determined by determining whether or not the level of the cavitation level signal Sc is greater than a threshold value that is close to 0. Further, the cavitation generation level can also be precisely detected even in a case in which, during an operation, the surgeon changes the setting value from the setting section 24 so as to change the output level of the drive signal.

In contrast, according to the related art example it is necessary to previously set a threshold value for detecting generation of a cavitation, and it is considered that it is necessary to change the threshold value in a case in which the output of the drive circuit is changed.

The related art example further discloses a configuration that is provided with a microphone that detects the continuous sound of a frequency that is generated at the time of a cavitation, in which cavitation suppression is performed with an audio signal that the microphone outputs.

However, in this case it is necessary to provide the microphone at a distal end side of an elongated probe 2*a* that can be inserted into the body.

In contrast, according to the present embodiment, the existence/non-existence of cavitation generation and the generation level can be detected on the side of the ultrasound driving apparatus 5 that is disposed outside the body. Further, with respect to the configuration of the probe itself, an existing probe and handpiece can be employed.

Accordingly, the present embodiment has a merit of easy application even in the case of an existing handpiece that includes a transducer.

In this connection, as a detection section that detects cavitations, a configuration may be adopted which, for example, detects a signal of a subharmonic component excluding the resonance frequency f res.

Figure 8:
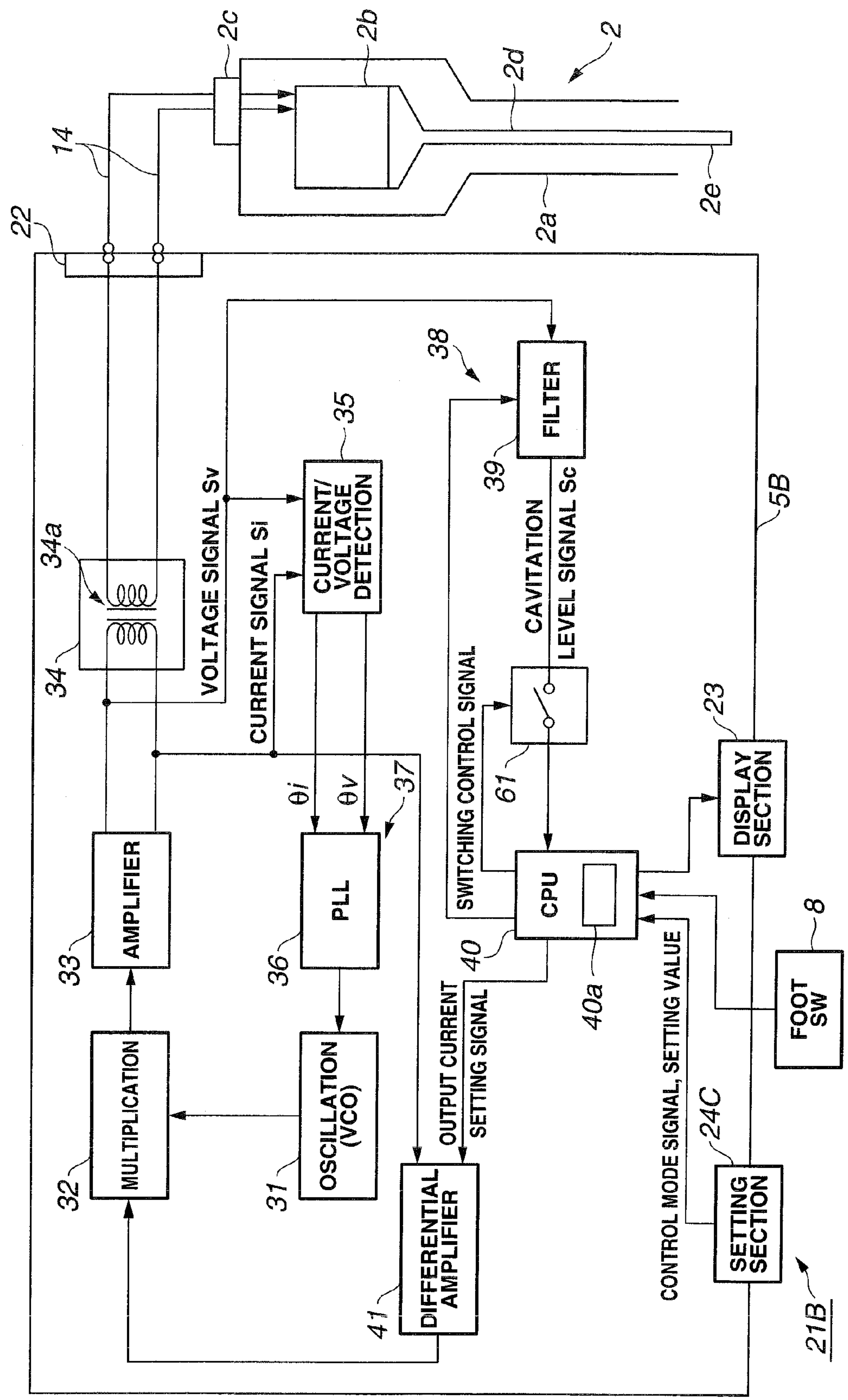
FIG. 8 is a configuration diagram of an ultrasound operation apparatus according to a second embodiment of the present invention.

FIG. 8 is a view that illustrates a configuration of an ultrasound operation apparatus 21B according to a modification example. The ultrasound operation apparatus 21B includes an ultrasound driving apparatus 5B that is in accordance with the ultrasound driving apparatus 5 of the ultrasound operation apparatus 21 shown in FIG. 3, and is further provided with a relay device 61 that switches between the filter circuit 39 and the CPU 40 using a switching control signal.

The relay device 61 is switched on/off by a switching control signal from the CPU 40 to thereby switch the control mode. More specifically, the CPU 40 further includes a control switching section that switches the control mode.

Figure 9:
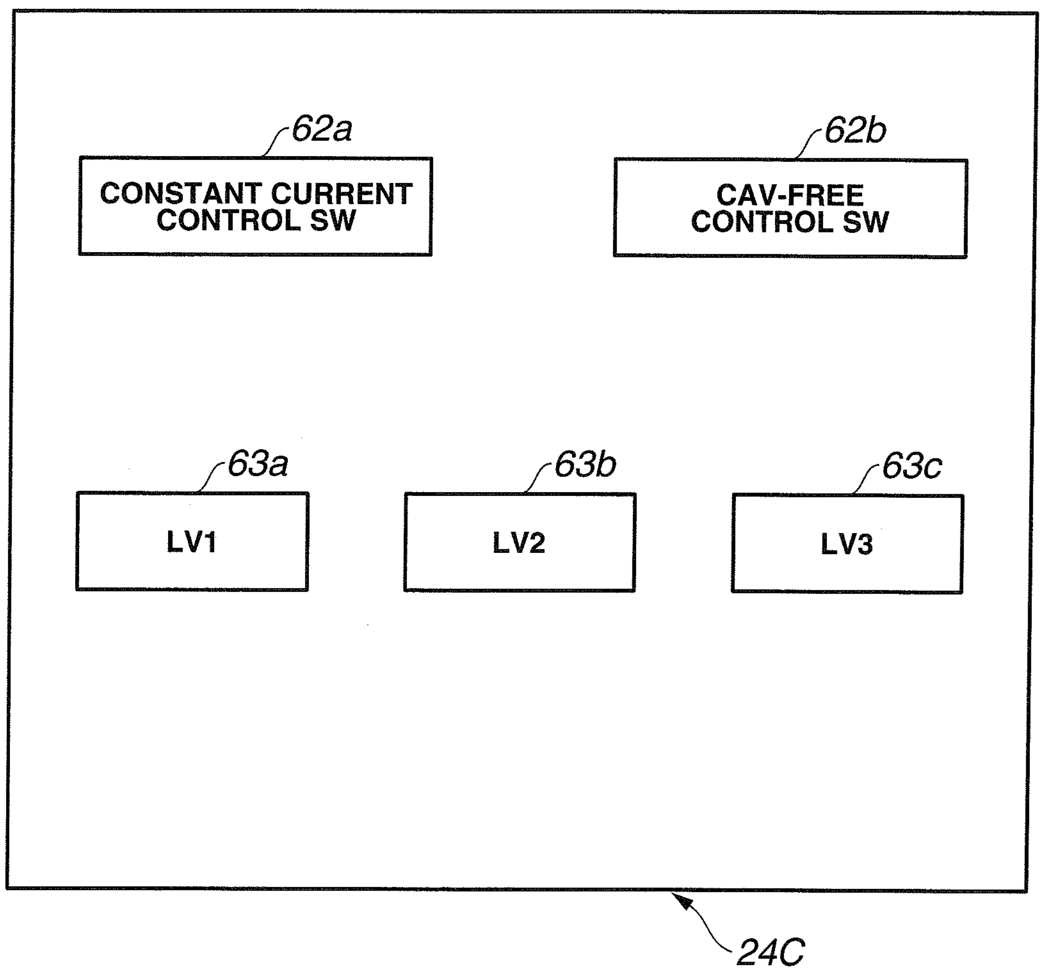
FIG. 9 is a view that illustrates a setting section that selectively sets a plurality of control modes.

Further, the ultrasound driving apparatus 5B, for example, includes a setting section 24C as shown in FIG. 9.

The setting section 24C is provided with a constant current control switch 62*a* with which the surgeon selectively designates the constant current control mode and a cavitation-free control switch 62*b* with which the surgeon selectively designates the cavitation-free control mode.

The setting section 24C is also provided with level switches 63*a*, 63*b*, and 63*c* that set an output level in the case of both control modes to a plurality of levels. For example, the level switches 63*a*, 63*b*, and 63*c* set an output level to LV1, LV2, and LV3, respectively.

Accordingly, the setting section 24C outputs to the CPU 40 a control mode signal that designates the constant current control mode or the cavitation-free control mode, and a setting value that sets the output level.

In this connection, although FIG. 9 illustrates a configuration in which level switches 63*j* (j=a to c) are commonly used when setting a level in both control modes, a configuration may also be adopted in which two sets dedicated to the respective control modes are provided that each include, for example, a plurality of level switches.

In the configuration shown in FIG. 8, the CPU 40 performs output control in accordance with the control mode setting that is made at the setting section 24C by the surgeon.

More specifically, when the constant current control mode is selected, the CPU 40 outputs a switching control signal that switches the relay device 61 to "off". Subsequently, the CPU 40 outputs an output current setting signal to the differential amplifier 41 so as to maintain the output level according to the level switches 63*j* (j=a to c) at the setting section 24C.

In contrast, when the cavitation-free control mode is selected, the CPU 40 outputs a switching control signal that switches the switch of the relay device 61 to "on". Accordingly, a cavitation level signal Sc from the filter circuit 39 is inputted to the CPU 40 via the relay device 61 that has been switched "on".

Subsequently, the CPU 40 controls so as to maintain the output level according to the level switches 63*j* in a state that maintains a state in which the cavitation level signal Sc is 0.

The remaining configuration is the same as that of the first embodiment shown in FIG. 3. Further, since the operations of the present modification example are almost the same as in the case described with FIG. 6 and FIG. 7, a description of the operations is omitted here.

Second Embodiment

Figure 10:
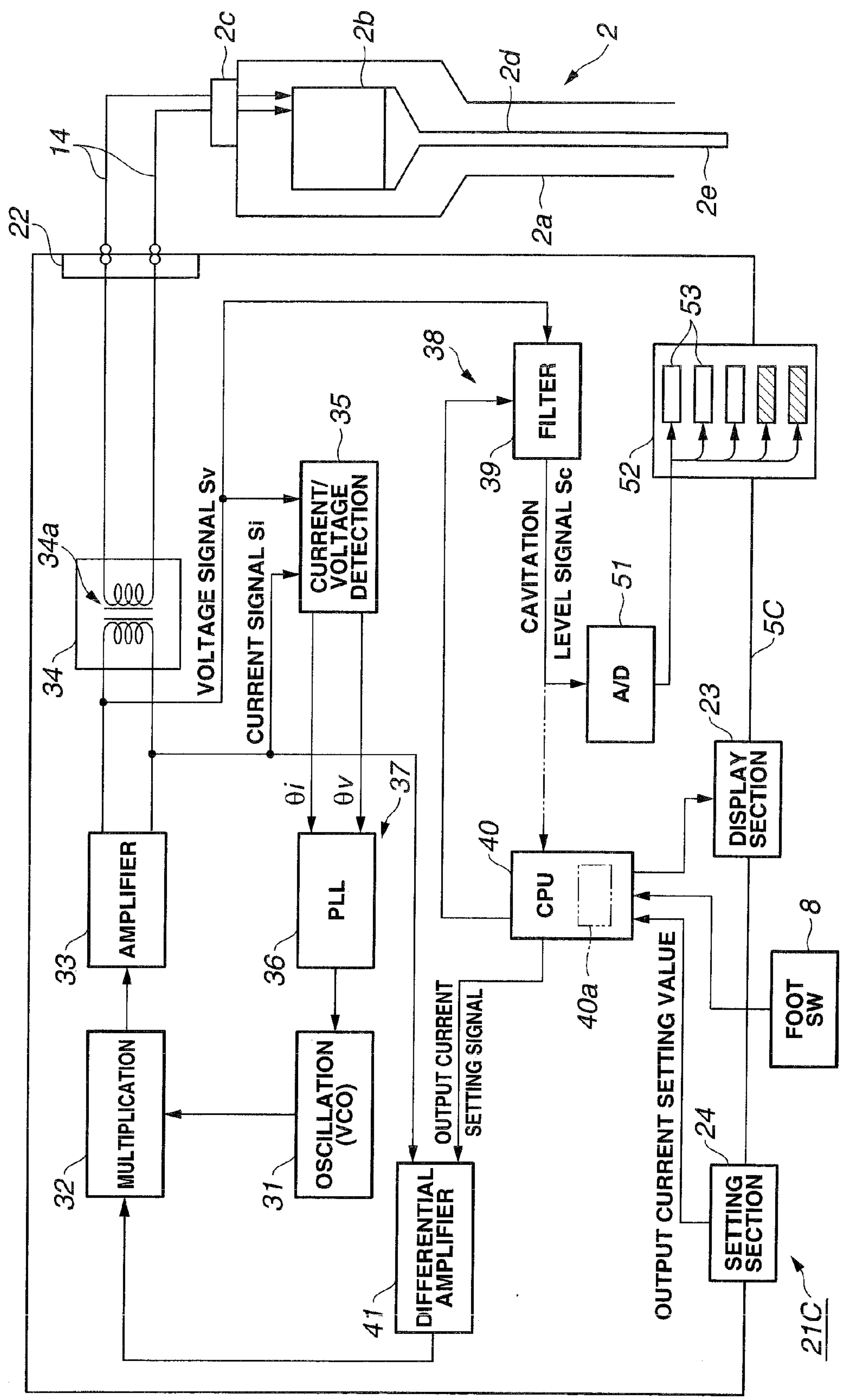
FIG. 10 is a configuration diagram of an ultrasound operation apparatus according to a third embodiment of the present invention.

Next, a second embodiment of the present invention is described with reference to FIG. 10. FIG. 10 is a view that shows the configuration of an ultrasound operation apparatus 21C according to a second embodiment of the present invention. In the first embodiment, an apparatus and method are described that perform automatic control so as to eliminate the generation of cavitations in the cavitation-free control mode.

In contrast, the present embodiment has a configuration that includes a notification section that notifies a cavitation generation level to the surgeon as a user by quantitatively displaying the generation level. Further, the configuration allows the surgeon to manually set a setting value of the setting section 24 so as to set a desired cavitation level from the displayed generation level.

The ultrasound operation apparatus 21C has an ultrasound driving apparatus 5C that includes, in the configuration of the ultrasound driving apparatus 5 shown in FIG. 3, an A/D conversion circuit 51 that subjects an output signal of the filter circuit 39 to A/D conversion, and an indicator 52 as a notification section that quantitatively displays an cavitation generation level by means of an output signal of the A/D conversion circuit 51.

In this connection, according to the present embodiment the CPU 40 does not have the cavitation generation control section 40*a*. As a modification example of the present embodiment, a configuration may be adopted in which, as indicated by the chain double-dashed line, the cavitation level signal Sc is inputted to the CPU 40, and a selection can be made also of a control mode that suppresses cavitation as in the first embodiment. Therefore, the cavitation suppression control section 40*a* is indicated with a chain double-dashed line in FIG. 8.

A cavitation level signal Sc that is outputted from the filter circuit 39 is subjected to A/D conversion by the A/D conversion circuit 51. The digital signal that has undergone A/D conversion corresponds to the cavitation generation level.

Subsequently, for example, a plurality of LEDs 53 that constitute an indicator 52 are caused to emit light by the digital signal. For example, the number of LEDs 53 that emit light changes approximately in proportion to the cavitation generation level. In FIG. 10, for example, two LEDs 53 are emitting light, as indicated by the diagonal lines. When the cavitation generation level increases further, more of the LEDs 53 emit light.

In this connection, in the present embodiment an output current setting value that is set by the surgeon is inputted to the CPU 40 from the setting section 24, and the CPU 40 outputs to the differential amplifier 41 an output current setting signal corresponding to the output current setting value so as to maintain the output current setting value from the setting section 24.

In the present embodiment, a drive signal that is supplied to the transducer 2*b* (more generally, a transducer Ib) is subjected to output control so as to maintain the output current setting value.

That is, the CPU 40 performs output control according to the constant current control mode as described in the first embodiment. The remaining configuration is the same as in the first embodiment.

According to the present embodiment, the surgeon can check the cavitation generation level using the display of the number of LEDs 53 emitting light on the indicator 52. When the surgeon checks the cavitation generation level and wishes to decrease the cavitation generation level further, it is sufficient for the surgeon to lower the output current setting value. Further, when the surgeon does not want to allow the generation of cavitations, it is sufficient to lower the output current setting value even further. Thus, the surgeon can perform treatment after setting an output current setting value that facilitates treatment.

According to the present embodiment, the surgeon can refer to the indicator 52 that notifies the surgeon of the cavitation generation level by means of a display, and treatment can be performed using a setting value desired by the surgeon. In this connection, apart from notifying the surgeon using a display device, the notification section may be configured, for example, to notify the surgeon with a sound or the like.

A configuration may also be adopted in which the function of the notification section of the indicator 52 is provided in the display section 23. For example, in the embodiments described after FIG. 11, although the indicator 52 is not shown, the function of the indicator 52 may be performed by the display section 23. Further, in the first embodiment also, a configuration may be adopted in which the display section 23 includes the notification section.

In this connection, for the second embodiment shown in FIG. 10, a configuration may also be adopted in which, as indicated by the chain double-dashed line, the cavitation level signal Sc of the filter circuit 39 is also inputted to the CPU 40 so that, by monitoring the existence/non-existence of cavitation generation, a setting can be more rapidly performed to change from a state in which cavitations are generated to a level at which cavitations are not generated.

Cavitations exhibit hysteresis characteristics, and once cavitations are generated, in some cases cavitations exhibit characteristics such that the cavitations do not cease even if the setting level of a drive signal is lowered as far as the output level that existed immediately prior to generation of the cavitations.

Figure 11:
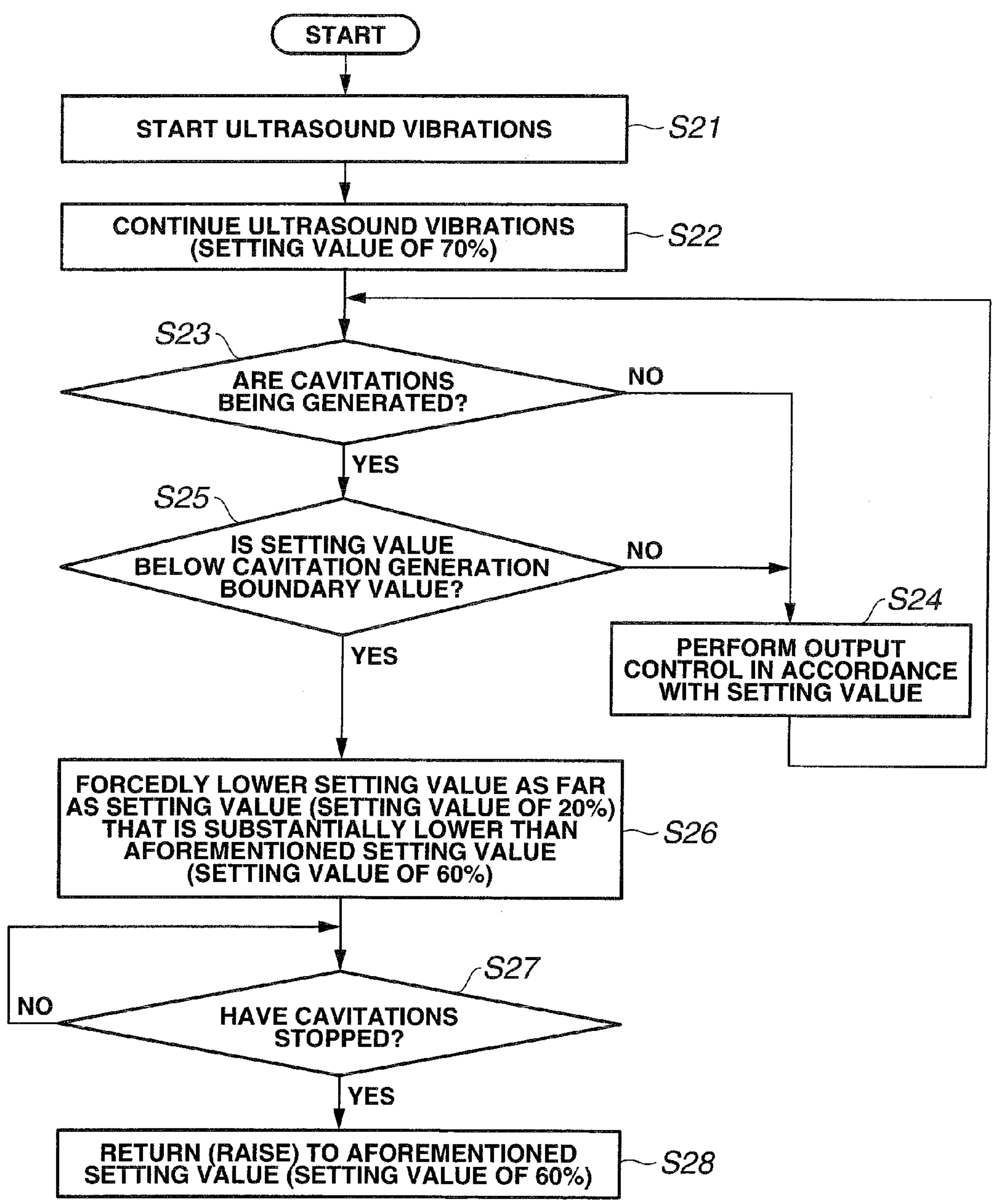
FIG. 11 is a flowchart that illustrates a suppression method that lowers an ultrasound output from a cavitation generation state.

Therefore, by employing a cavitation control method as shown in FIG. 11, the drive signal can be set to an output level such that the generation of cavitations ceases with good responsiveness and in a short time.

In the initial step S21, the transducer 2*b* and the distal end member 2*e* of the handpiece 2 start to generate ultrasound vibrations. Next, in step S22, the ultrasound vibrations continue, for example, at 70% of the maximum setting value (abbreviated to "setting value of 70%").

In this case, as shown in step S23, the CPU 40 determines the existence/non-existence of cavitation generations based on the output signal of the filter circuit 39.

When it is determined in step S23 that cavitations are not being generated, the CPU 40 proceeds to the processing of step S24 to perform output control corresponding to a setting value that is set at the setting section 24 by the surgeon. The CPU 40 then returns to the processing of step S23. That is, in a case in which cavitations are not being generated, the CPU 40 performs output control so as to maintain a setting value that corresponds to a setting value that is manually set by the surgeon.

In contrast, when it is determined that cavitations are being generated, the CPU 40 proceeds to the processing of step S25. In step S25, the CPU 40 determines whether or not the surgeon lowered the setting value as far as a setting value (for example, assumed to be a setting value of 60%) that is below a cavitation generation boundary value.

In a case in which the surgeon changes the setting value within a range that does not stop cavitation generation (that is, changes a setting value while keeping a state in which cavitations are generated), the CPU 40 returns to the processing of step S23 via step S24.

In contrast, in a case in which the surgeon has performed a setting that lowers the setting value to a setting value (the aforementioned setting value of 60%) that is below the cavitation generation boundary value, as shown in step S26, the CPU 40 forcedly lowers the setting value to a setting value (for example, setting value of 20%) that is substantially lower than that setting value.

That is, even in a case in which cavitations exhibit hysteresis characteristics, the setting value is forcedly (temporarily) lowered as far as a setting value at which the generation of cavitation rapidly ceases.

In this state, as shown in step S27, the CPU 40 monitors the output signal of the filter circuit 39 and waits until the cavitations cease (in a case in which the CPU 40 can monitor the output signal of the filter circuit 39).

After the cavitations ceased, as shown in step S28, the CPU 40 returns the setting value from the forcedly lowered setting value to the setting value that has been set by the surgeon (the aforementioned setting value of 60%).

By performing this control, when the surgeon changes and sets the drive signal to a setting value that stops cavitations in a state in which cavitations have been generated, even when the cavitations exhibit hysteresis characteristics a setting can be made that eliminates the cavitations in a short time to enter a state in which output is performed at the setting value that is set by the surgeon.

Although according to the above embodiment an operational flow is described in which the processing of step S26 is performed after the operation by the surgeon in step S25, a configuration may also be adopted in which automatic control is performed so as to move to step S26 automatically once generation of cavitations is detected, without the operation in step S25.

In this connection, instead of the CPU 40 making a decision to wait until cavitations cease in step S27 of FIG. 11, a configuration may also be adopted in which the CPU 40 waits until the lapse of a fixed time. As the fixed time in this case, for example, it is sufficient to set a time in which a margin is included in addition to a time required for cavitations to cease. This case can be applied to a case of a configuration that does not monitor the output signal of the filter circuit 39.

Figure 12:
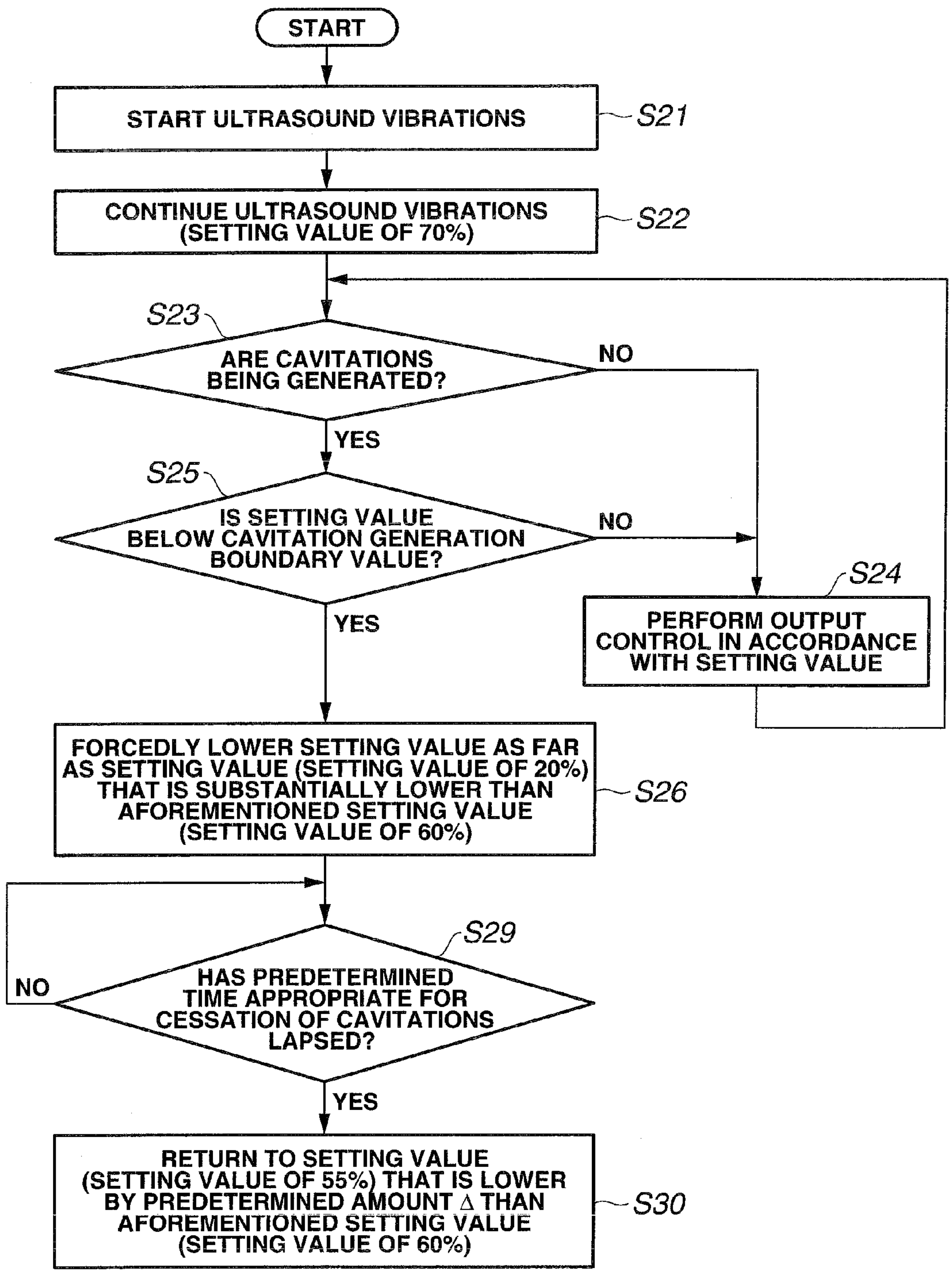
FIG. 12 is a flowchart that illustrates another suppression method that lowers an ultrasound output from a cavitation generation state.

In consideration of the fact that cavitations exhibit hysteresis characteristics, a control method as shown in the flowchart illustrated in FIG. 12 may also be adopted by the ultrasound operation apparatus 21C according to the second embodiment.

FIG. 12 is a flowchart that includes the same control procedures as shown in FIG. 11 from step S21 to step S26. After step S26, as shown in step S29, the CPU 40 waits for a predetermined time that is required for cavitations to cease to elapse. In this connection, step S27 shown in FIG. 11 may be employed in place of step S29.

Thereafter, as shown in step S30, the CPU 40 returns (raises) the setting value to a value (setting value of 55%) that is smaller by a predetermined amount Δ (for example, a setting value of 5%) than the above described setting value (setting value of 60%).

The predetermined amount Δ in this case is a value that is set in correspondence with the hysteresis characteristics. The predetermined amount Δ may also be appropriately set in accordance with a change amount in a case in which a setting value is changed from a setting value in a state in which hysteresis actually occurs to a setting value that causes the generation of cavitations to stop, or in accordance with the level of cavitations that are initially generated or the like. Further, a configuration may be adopted in which the apparatus is actually used and a value that is set based on results obtained by actual use is set as the predetermined amount Δ.

According to the control method illustrated in FIG. 12, even in a case in which cavitations are generated and the cavitations exhibit hysteresis characteristics, it is possible to rapidly set an output state that is desired by the surgeon.

As described above, the control methods shown in FIG. 11 and FIG. 12 can be widely used when stopping (or eliminating) cavitation generation from a state in which cavitations have been generated. The control methods can also be utilized in the case of suppressing the generation of cavitations in a short time.

Further, as the control method of the modification example shown in FIG. 12, a configuration may be adopted in which, instead of step S25, the CPU 40 determines whether or not control has been switched to a setting that suppresses cavitations. Thus, a configuration may be adopted such that the CPU 40 moves to step S26 in a case in which control has been switched to a setting that suppresses cavitations by the setting section 24C, and the CPU 40 moves to step S24 when the control has not been switched.

Further, after cavitations were generated, in a case in which the setting value has not been lowered to a setting value below the aforementioned boundary value (in some cases this value has a width) at which cavitations are generated, the control method shown in FIG. 12 or a control method that is a modified version thereof may be adopted.

For example, in a state in which cavitations are being generated, when a cavitation detection signal level in a case in which the cavitation-free control switch 62*b* has been operated is, for example, a first predetermined level, the CPU 40 may be configured to perform output control so that the cavitation detection signal level becomes a second level that is lower than the first predetermined level, as in step S26.

Third Embodiment

Next, a third embodiment of the present invention is described referring to FIG. 13. According to the present embodiment a configuration is adopted in which the control mode can be automatically set in accordance with the handpiece I or probe Ia that is actually used.

FIG. 13 illustrates the configuration of an ultrasound operation apparatus 21D as the third embodiment. As described hereunder, the present embodiment example is provided with an identification section that identifies a handpiece I, and is configured to be capable of switching the control mode in accordance with the identification result.

The ultrasound operation apparatus 21D is according to, for example, the ultrasound operation apparatus 21B shown in FIG. 8, in which each handpiece I (in FIG. 13, I=2), for example, includes a ROM Ih that forms an identifier that generates handpiece classification information (also referred to simply as "classification signal") that is contained, for example, in the proximal end section of the probe Ia.

Further, an ultrasound driving apparatus 5D includes a communication circuit 66 that reads out a handpiece classification signal that is stored in the ROM Ih from the handpiece I that is connected via the ultrasound cable 14 to the ultrasound driving apparatus 5D. The communication circuit 66 sends the handpiece classification signal that is read out to the CPU 40.

The CPU 40 can identify the type of handpiece I, the type of transducer Ib mounted to the handpiece I, and the shape or state of the distal end section of the probe Ia of the handpiece I and the like based on the handpiece classification signal from the communication circuit 66.

In accordance with the handpiece classification signal, the CPU 40, for example, refers to information stored in a flash memory 67 to automatically select and set one of the constant current control mode and the cavitation-free control mode.

Information that indicates which control mode to use in correspondence with a handpiece classification signal is previously stored in the flash memory 67. In this connection, the information stored in the flash memory 67 can be changed or updated, for example, from the setting section 24C via the CPU 40.

For example, in a case in which the handpiece 2 is connected to the ultrasound driving apparatus 5D, the CPU 40 selects the cavitation-free control mode by referring to the corresponding information. In contrast, when the handpiece 3 is connected to the ultrasound driving apparatus 5D, the CPU 40 selects the constant current control mode by referring to the corresponding information.

Further, in a case in which information that indicates that the control mode is to be set (selected) manually from the setting section 24C is stored in the flash memory 67, the CPU 40 preferentially sets the control mode that is selected manually by the surgeon from the setting section 24C.

In this connection, the present embodiment is not limited to a case in which respective handpiece classification signals are stored in the ROM Ih. A configuration may also be adopted in which the manufacturer's serial numbers of handpieces are stored in the ROM Ih, and the CPU 40 refers to a manufacturer's serial number that is stored in the flash memory 67 to identify the classification of the corresponding handpiece or the like.

The present embodiment is not limited to a case that uses the ROM Ih, and for example, a configuration may be adopted in which identification is performed using a resistance value, or in which the type of handpiece or the like can be identified based on an on/off array of, for example, DIP switches that include a plurality of switching elements.

Figure 14:
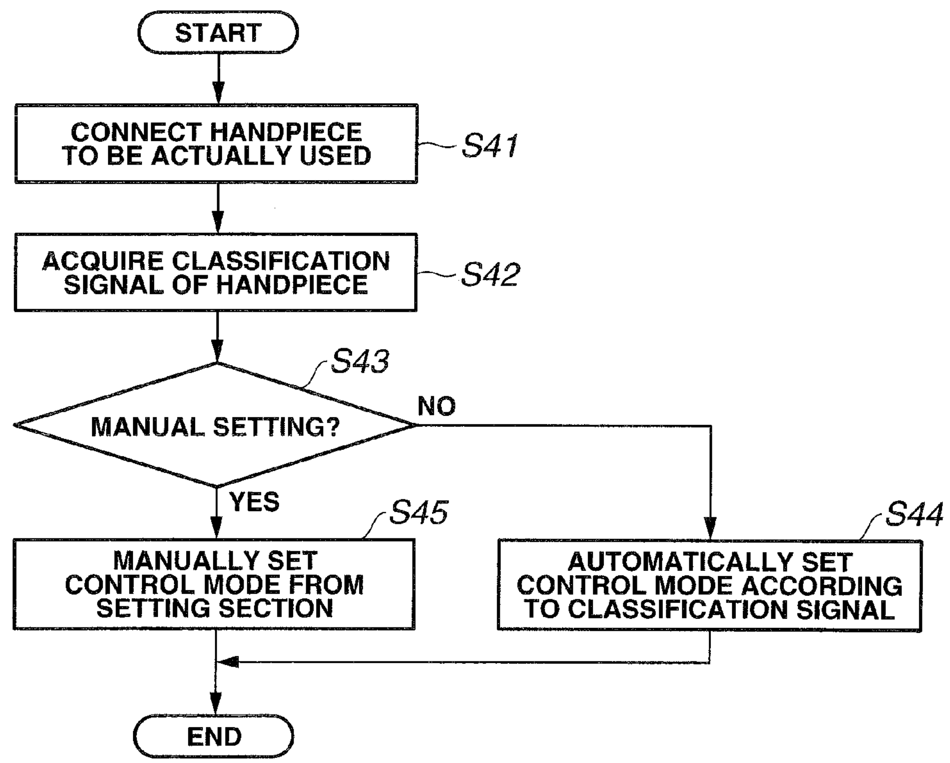
FIG. 14 is a flowchart illustrating a control method according to the first modification example.

Next, the operation of the present embodiment is described referring to the flowchart shown in FIG. 14.

As shown in step S41, the surgeon connects the handpiece I to be actually used to the ultrasound driving apparatus 5D, and turns on the power of the ultrasound driving apparatus 5D.

Thereupon, as shown in step S42, the CPU 40 acquires a classification signal of the handpiece I from the ROM Ih of the handpiece I via the communication circuit 66. That is, the CPU 40 identifies the type of handpiece I.

Next, as shown in step S43, the CPU 40 refers to information stored in the flash memory 67 to determine based on the classification signal if, for example, a manual setting is to be performed.

As shown in step S44, in a case in which a manual setting is not to be performed, that is, in a case in which the setting is to be performed automatically, the CPU 40 automatically sets the control mode according to the classification signal. In other words, the CPU 40 automatically selects or automatically switches a single control mode among a plurality of control modes in accordance with an identification result from the identification section.

In contrast, as shown in step S45, in the case of manual setting, the CPU 40 sets the control mode in accordance with a manual selection from the setting section 24C. Thus, the operation to set the control mode ends. Following this operation to set the control mode, for example, after the initial settings, the operations similar to those of step S2 in FIG. 6 are performed.

According to the present embodiment, once the surgeon pre-registers information regarding control modes that the surgeon desires to use in accordance with the classification of handpieces in the flash memory 67, thereafter a single control mode is automatically set from among a plurality of control modes in accordance with the pre-registered information. Thus, the ease of operation with respect to treatment performed by the surgeon can be enhanced.

The surgeon can also preferentially select the constant current control mode or the cavitation-free control mode manually from the setting section 24C and perform treatment.

FIG. 15 is a view that illustrates a configuration of an ultrasound operation apparatus 21E according to a first modification example.

The ultrasound operation apparatus 21E includes an ultrasound driving apparatus 5E that is in accordance with the ultrasound driving apparatus 5D of the ultrasound operation apparatus 21D shown in FIG. 13, with the exception that the ultrasound driving apparatus 5E does not have the relay device 61. In this case the cavitation level signal Sc of the filter circuit 39 is inputted to the CPU 40.

The CPU 40 refers to the cavitation level signal Sc that is in accordance with a control mode set according to the handpiece classification signal or a control mode selected (set) from the setting section 24C.

The operations of the present modification example are approximately the same as the operations in the case of the configuration in FIG. 13. An operation that is different to the case of the configuration shown in FIG. 13 is that the cavitation generation level can be displayed on the display section 23 even in a state in which the constant current control mode is set.

Further, for example when adopting the control described in FIG. 11, by monitoring the cavitation level signal Sc an output level can be set that stops the generation of cavitations in a state in which there is good responsiveness.

Figure 16:
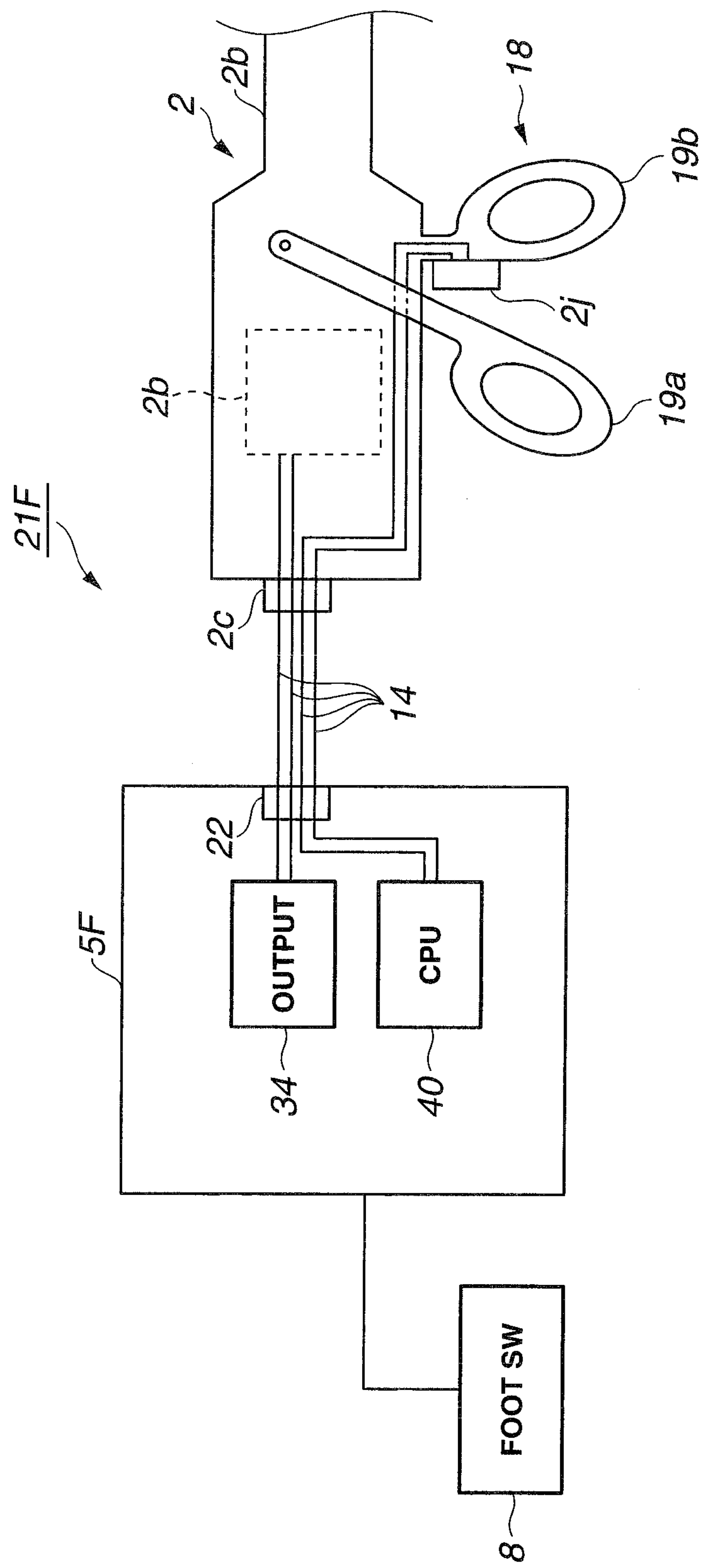
FIG. 16 is a view that shows an outline of principal parts of an ultrasound operation apparatus according to a third modification example.

FIG. 16 is a view that illustrates an outline configuration of principal parts of an ultrasound operation apparatus 21F according to a second modification example. The present modification example is configured to be capable of detecting a change in a usage state in a specific treatment instrument to automatically switch a control mode.

The surgeon normally places the distal end members 2*e* and 2*g* in a closed state to perform coagulation/dissection treatment. At such time, there are many cases in which the surgeon desires to perform treatment with suppressing cavitations. Further, when coagulation/dissection treatment is performed with the distal end members 2*e* and 2*g* in an open state, exfoliating dissection treatment is performed. At such time, there are many cases in which the surgeon wants cavitations to be generated.

The ultrasound operation apparatus 21F includes an ultrasound driving apparatus 5F that is, for example, in accordance with the ultrasound driving apparatus 5E of the ultrasound operation apparatus 21E shown in FIG. 15, with the exception that the ultrasound driving apparatus 5F does not include the communication circuit 66 provided in the ultrasound driving apparatus 5E, and that a detection signal from a sensor 2*j* provided in a specific handpiece 2 is inputted to the CPU 40.

As shown in FIG. 16, for example, the sensor 2*j* that is switched "on" from an "off" state by a pressing force is mounted at a position facing a moveable handle 19*a* on a fixed handle 19*b* in the handpiece 2.

The sensor 2*j* detects an open/closed state of the handle 18 and, for example, outputs an "on" detection signal when the handle 18 is in a closed state and outputs an "off" detection signal when the handle 18 is in an open state.

The distal end members 2*e* and 2*g* on the distal end side of the probe 2*a* open and close in accordance with an open/closed state of the handle 18. Accordingly, the sensor 2*j* outputs a signal that has detected an open/closed state of the distal end section (distal end members 2*e*, 2*g*).

The CPU 40 switches the control mode in accordance with the detection signal of the sensor 2*j* that detects the open/closed state of the distal end section by means of opening/closing of the handle 18. In this connection, information relating to switching the control mode in accordance with a detection signal of the sensor 2*j* is, for example, stored in the flash memory 67.

Figure 17:
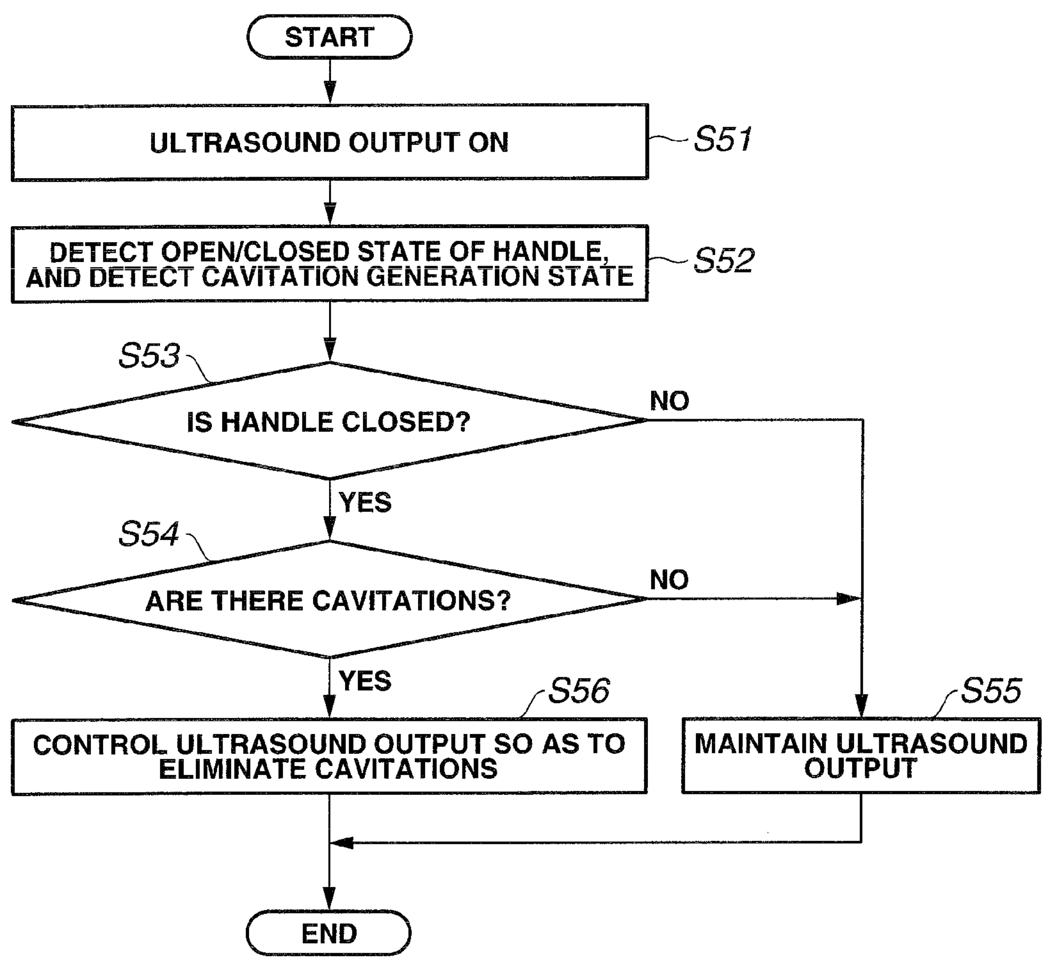
FIG. 17 is a flowchart that illustrates a control method according to the third modification example.

FIG. 17 is a view that illustrates a flowchart of operations according to the present modification example. After the power supply of the ultrasound driving apparatus 5F has been turned on, when the foot switch 8 is switched "on", ultrasound is outputted as shown in step S51.

More specifically, the transducer 2*b* generates ultrasound vibrations upon application of a drive signal to the transducer 2*b*, the ultrasound vibrations are transmitted to the distal end member 2*e*, and the distal end member 2*e* makes ultrasound vibrations (abbreviated as "ultrasound is outputted").

As shown in step S52, the CPU 40 detects opening/closing of the handle 18 based on the detection signal of the sensor 2*j* and detects a cavitation generation state based on the output signal of the filter circuit 39.

In step S53, the CPU 40 determines whether or not the handle 18 is closed. The surgeon, for example, opens the handle 18 (the distal end section opens also) to perform exfoliating dissection treatment, while the surgeon closes the handle 18 to perform coagulation/dissection treatment.

If the handle 18 is closed the CPU 40 proceeds to step S54, and if the handle 18 is open the CPU 40 proceeds to step S55.

In step S54, the CPU 40 determines whether or not cavitations are generated (abbreviated to "is there a cavitation"). When the determined result is that there are no cavitations, the CPU 40 proceeds to step S55.

In step S55, the CPU 40 maintains the state of the immediately preceding ultrasound output. The surgeon continues to perform treatment by ultrasound in that ultrasound output state.

In contrast, when the determined result in step S54 is that there are cavitations, as shown in step S56, the CPU 40 controls output of ultrasound so as to eliminate the cavitations using a function of the cavitation suppression control section 40*a*. That is, the CPU 40 performs control to set a cavitation-free state.

Thus, according to the present modification example, in a case in which the distal end section has been closed, when cavitations are being generated the CPU 40 controls so as to suppress (including reducing or stopping output) cavitations, and when cavitations are not being generated the CPU 40 controls so as to maintain ultrasound output in the same output state.

In other words, in a case in which the handle 18 is closed and there are cavitations, the CPU 40 switches to a control mode so as to eliminate the generation of cavitations.

In this connection, a configuration may also be adopted in which, when there are cavitations in step S54, the CPU 40 controls so as to eliminate the generation of cavitations after a fixed time. Furthermore, when using the handpiece 2 with, as shown in FIG. 1, the ultrasound driving apparatus 5 together with the high frequency output apparatus 6, in a case in which living tissue that is treated by friction produced by ultrasound undergoes carbonized denaturation to a certain degree, the high-frequency impedance changes.

A configuration may also be adopted that monitors the state of change in the high-frequency impedance and reduces or stops the output of ultrasound if the carbonized denaturation has proceeded to a certain degree and coagulation treatment has been performed.

In this connection, if it is determined in step S53 that the handle 18 is not closed, i.e. that the handle 18 is open, ultrasound output is maintained as shown in step S55.

The control method according to FIG. 17 facilitates performance of this kind of treatment, and can improve the ease of operation for the surgeon with respect to treatment.

According to the present modification example, since a configuration is adopted that changes the output control of a drive signal in accordance with a usage state of the handpiece 2, it is possible to reduce the time and trouble required for a surgeon to perform an operation to change the output while performing treatment.

That is, the present modification example can enhance the ease of operation with respect to an ultrasound operation.

Fourth Embodiment

Figure 18:
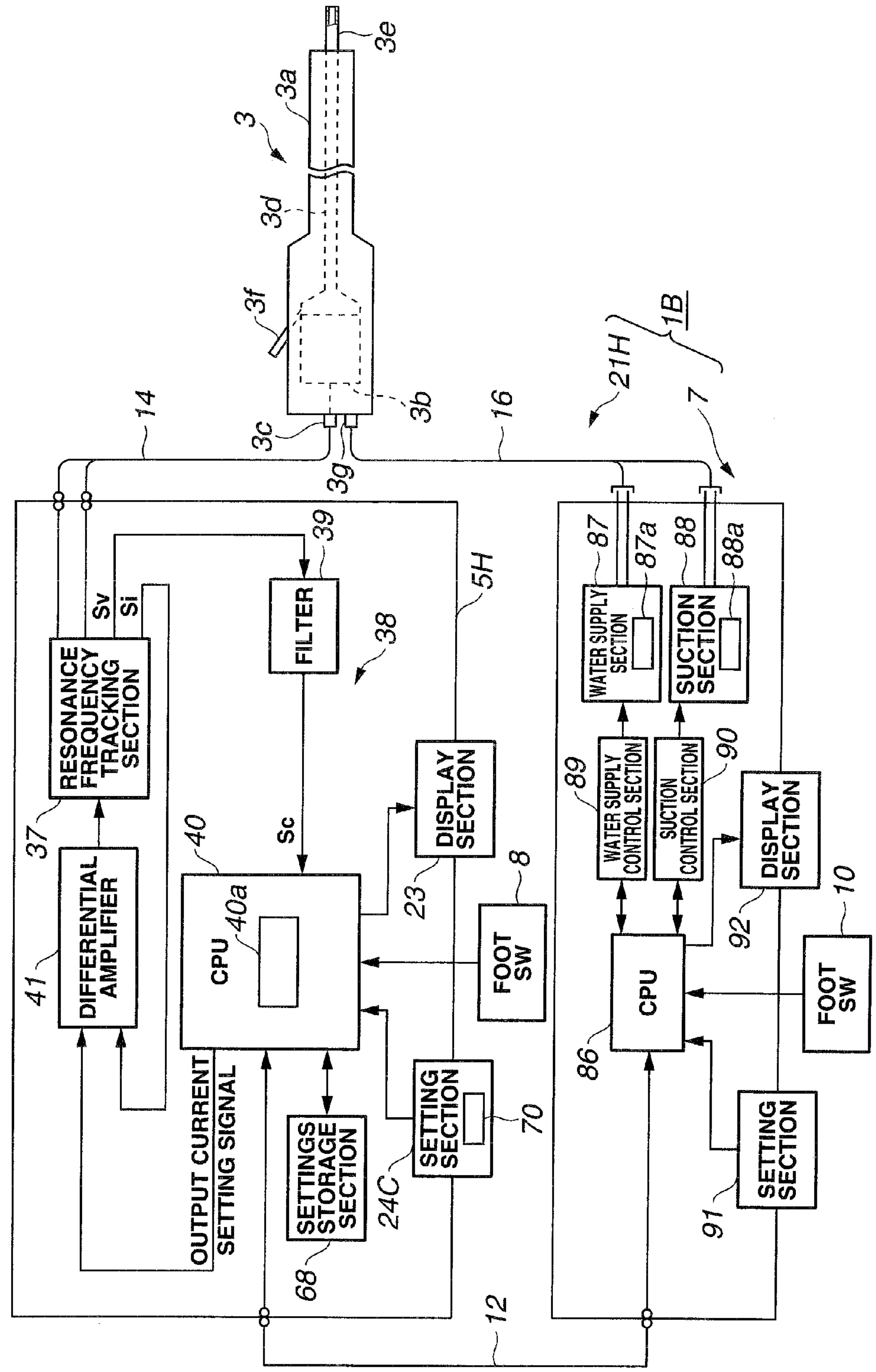
FIG. 18 is a block diagram that illustrates a configuration of an ultrasound operation system including a fourth embodiment of the present invention.

Next, a fourth embodiment of the present invention will be described referring to FIG. 18. FIG. 18 illustrates a configuration of an ultrasound operation system 1B that includes the fourth embodiment. The present embodiment monitors a suction amount that is actually sucked with respect to a preset suction amount when water supply and suction operations are made to operate in response to each other when performing treatment using ultrasound vibrations. When the actual suction amount is less than the suction amount that has been set, control is performed to eliminate (stop) cavitations or to reduce cavitations.

The ultrasound operation system 1B includes an ultrasound operation apparatus 21H of the fourth embodiment as well as a water supply/suction device 7 that is used simultaneously with the ultrasound operation apparatus 21H.

The ultrasound operation apparatus 21H includes an ultrasound driving apparatus 5H and the handpiece 3 that is connected to the ultrasound driving apparatus 5H and the water supply/suction device 7.

The CPU 40 included in the ultrasound driving apparatus 5H is connected via a communication cable 12 to a CPU 86 that is included in a control section of the water supply/suction device 7. The two CPUs 40 and 86 can perform two-way communication.

The ultrasound driving apparatus 5H is, for example, in accordance with the ultrasound driving apparatus 5E shown in FIG. 15 and, for example, has a configuration that does not include identification means (the ROM Ih, communication circuit 66, or flash memory 67) of the handpiece I. It should be noted that the present embodiment can also be applied to a configuration that includes identification means.

In FIG. 18, the components from the oscillating circuit 31 to the PLL circuit 36 are denoted by a resonance frequency tracking section 37 that is constituted by those components.

Furthermore, according to the ultrasound driving apparatus 5H of the present embodiment, the settings storage section 68 that stores information relating to setting values that are set at the setting section 24C and a setting section 91 of the water supply/suction device 7, for example, is constituted by a flash memory.

Further, the setting section 24C is provided with a storage button (or storage switch) 70 that performs an operation to instruct that setting value information be stored in the settings storage section 68.

The water supply/suction device 7 has a water supply section 87 that supplies water (the water in this case is, for example, physiological saline) and a suction section 88 that performs sucking, a water supply control section 89 and a suction control section 90 that control the operations of the water supply section 87 and the suction section 88, respectively, the CPU 86 as a control section that performs overall control of the water supply/suction device, a setting section 91 that sets a water supply amount and a suction amount and the like (i.e. performs a water supply amount setting and a suction amount setting), a display section 92 that displays a water supply amount and a suction amount and the like, and a foot switch 10 that performs operations to instruct that water supply or suction be performed.

In this connection, in FIG. 18, the CPU 86 may also be configured to fulfill the functions of the water supply control section 89 and the suction control section 90.

The water supply section 87 and the suction section 88 include therein a water supply pump 87*a* that constitutes a water supply drive section that supplies water and a suction pump 88*a* that constitutes a suction driving section that performs suction. The (water supply pump 87*a* of the) water supply section 87 and the (suction pump 88*a* of the) suction section 88 are connected to a water supply/suction connector 3*g* of the handpiece 3 via a water supply/suction tube 16 that includes a water supply tube and a suction tube that are respectively connected to a water supply connector and a suction connector.

When the surgeon operates the foot switch 10 to give an instruction to supply water, the CPU 86 drives the water supply pump 87*a* via the water supply control section 89. Thereupon, the water supply pump 87*a* pumps physiological saline to the vicinity of the living tissue that is the treatment target from the opening of the distal end member 3*e* via the water supply tube and the conduit inside the handpiece 3.

Further, when the surgeon operates the foot switch 10 to give an instruction to perform suction, the CPU 86 drives the suction pump 88*a* via the suction control section 90. Thereupon, the suction pump 88*a* sucks, via the suction tube, a liquid or fluid in which the liquid that has been supplied from the opening of the distal end member 3*e* and tissue pieces and the like that were crushed or ablated by the distal end member 3*e* are mixed.

The water supply amount by the water supply section 87 and the suction amount by the suction section 88 are detected by measuring the respective amounts using a flow rate sensor or the like inside the water supply section 87 and the suction section 88. The CPU 86 sets the level of a water supply drive signal and a suction drive signal that determine a water supply amount and a suction amount of the water supply pump 87*a* and the suction pump 88*a* in accordance with setting values from the setting section 91.

As described below, when performing treatment under a condition in which cavitations are suppressed, when it is detected that the suction amount (referred to as "set suction amount") that is set by the setting section 91 exceeds the actual suction amount, the CPU 40 performs control to decrease the cavitation output or stop (eliminate) cavitations.

Figure 19:
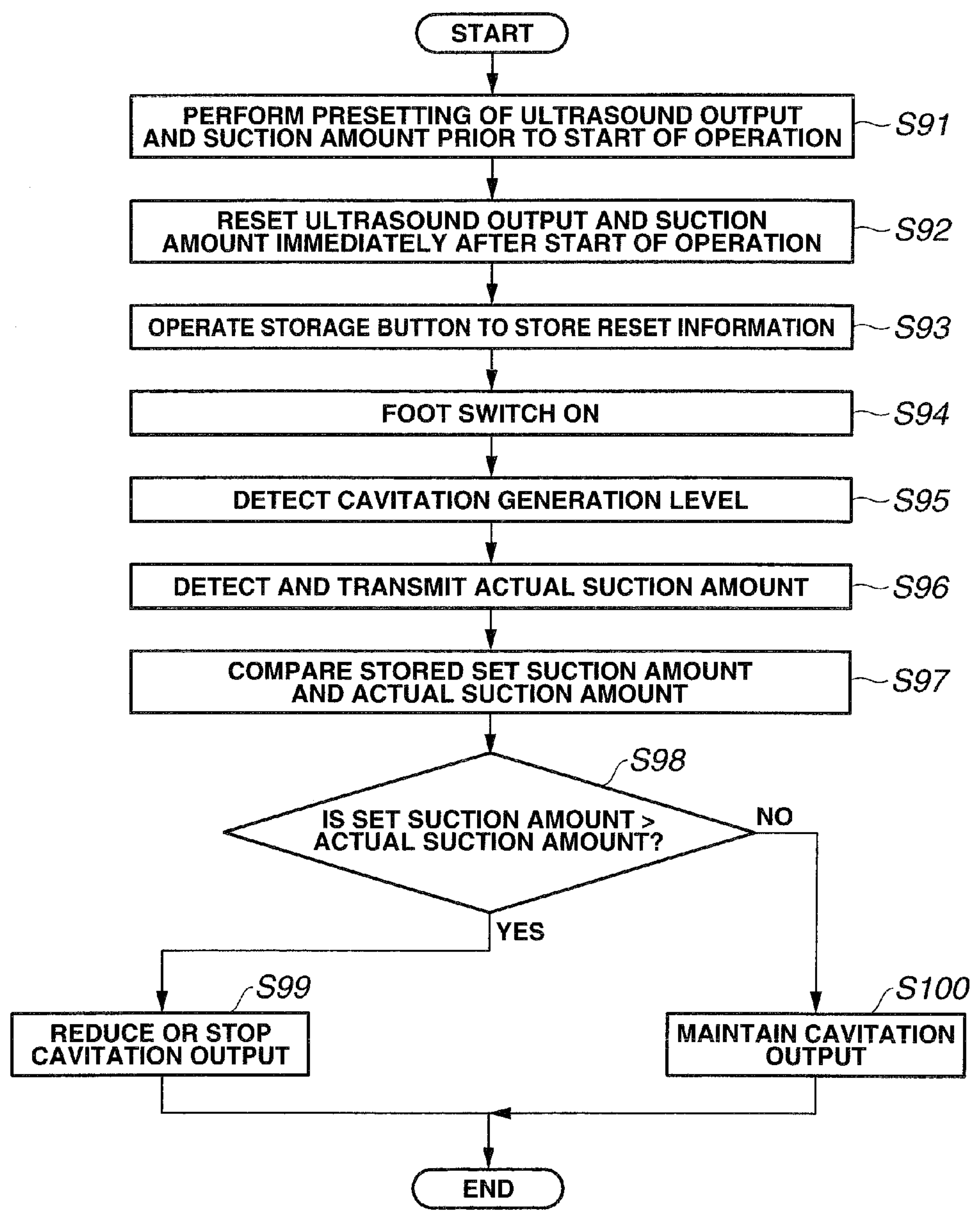
FIG. 19 is a flowchart that illustrates one example of a control method including cavitation suppression according to the fourth embodiment.

Next, operations including control that suppresses cavitations generated by the ultrasound operation system 1B are described referring to FIG. 19.

The surgeon connects the handpiece 3 to the ultrasound driving apparatus 5H and the water supply/suction device 7 as shown in FIG. 18, and turns on the power supply of the ultrasound driving apparatus 5H and the water supply/suction device 7. Next, the surgeon presets the ultrasound output and the suction amount and the like before starting an operation, as shown in step S91 of FIG. 19.

Subsequently, as shown in the next step S92, the surgeon resets the ultrasound output and the suction amount immediately after starting the operation. In step S92, the surgeon sets the ultrasound output and the suction amount to appropriate values that are suitable for the relevant case according to the state of the living tissue of the affected area on which treatment is to be performed as well as the preferences of the surgeon who is actually performing the operation and the like.

As shown in the next step S93, the surgeon then operates the storage button 70 to store information on the state that has been reset in step S92. By operating the storage button 70, information relating to the reset ultrasound output and suction amount is stored in the settings storage section 68 via the CPU 40.

Subsequently, as shown in step S94, the surgeon operates the foot switches 8 and 10 to activate the ultrasound driving apparatus 5H and the water supply/suction device 7.

Further, as shown in step S95, the CPU 40 detects the cavitation generation level based on the cavitation level signal Sc from the filter circuit 39. In this case, it is assumed that cavitations are being generated.

Next, as shown in step S96, the CPU 86 of the water supply/suction device 7 detects the actual suction amount. The CPU 86 sends the detected suction amount to the CPU 40 via the communication cable 12.

As shown in step S97, the CPU 40 compares the reset set suction amount that has been stored in the settings storage section 68 and the actual suction amount, and as shown in step S98, determines whether or not the set suction amount>the actual suction amount. In accordance with the determined result, the CPU 40 that performs cavitation suppression control suppresses cavitation.

When the result determined by the CPU 40 in step S98 is affirmative, in some cases the surgeon may desire to reduce or stop the cavitation output level in that state. Accordingly, in this case, as shown in step S99, the CPU 40 controls to reduce or stop the cavitation output.

In contrast, when the result determined by the CPU 40 in step S98 is negative, that is, when the set suction amount≤the actual suction amount, in some cases the surgeon may desire to maintain the cavitation output level in that state. Accordingly, in this case, as shown in step S100, the CPU 40 controls so as to maintain the current cavitation output.

According to the present embodiment, when the set suction amount exceeds the actual suction amount, control can be performed to reduce or stop the cavitation output.

Fifth Embodiment

Figure 20A:
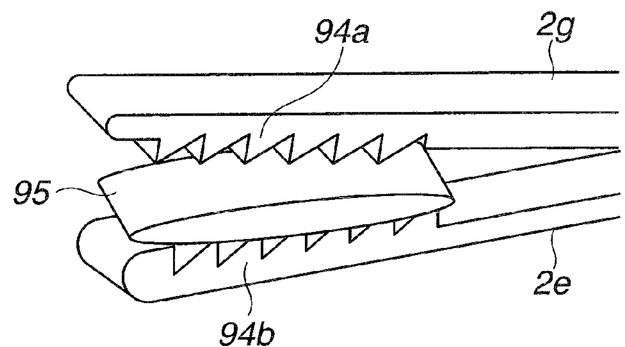
FIG. 20A is a view that illustrates a shape of a distal end section of a probe that is used in a fifth embodiment of the present invention.

Next, a fifth embodiment of the present invention is described referring to FIG. 20A and the like. FIG. 20A shows the shape of a distal end section of the handpiece 2 according to the fifth embodiment of the present invention. The distal end section of the handpiece 2 includes a moveable distal end member 2*g* and a fixed distal end member 2*e* that open/close in response to an opening/closing operation of the handle 18 (see FIG. 2).

According to the present embodiment, the moveable distal end member 2*g* and the fixed distal end member 2*e* are provided with sawtooth-shaped concavo-convex sections 94*a* and 94*b*, respectively, on opposing surfaces. The surgeon performs coagulation/dissection treatment by grasping a living tissue 95 as a treatment target between the two concavo-convex sections 94*a* and 94*b*.

By performing an operation to close the handle 18 from the state shown in FIG. 20A, the living tissue 95 is grasped between the concavo-convex section 94*a* of the moveable distal end member 2*g* and the concavo-convex section 94*b* of the fixed distal end member 2*e*, and enters a state in which the living tissue 95 is in close contact with a surface of each of the concavo-convex sections 94*a* and 94*b*.

Figure 20B:
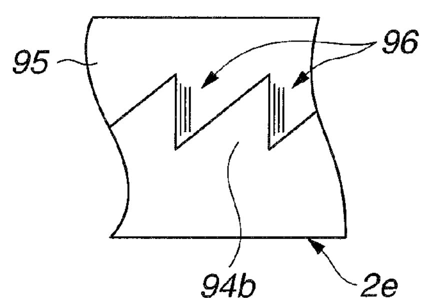
FIG. 20B is a view that illustrates a state in which a cavitation is produced by ultrasound vibrations of a concavo-convex section.

FIG. 20B is a view that shows a state in which the living tissue 95 is in close contact with the surface of the sawtooth-shaped concavo-convex section 94*b* of the fixed distal end member 2*e* that actually makes ultrasound vibrations. In this state, by causing the fixed distal end member 2*e* to make ultrasound vibrations, cavitations 96 may often be generated in the living tissue 95 in the vicinity of the surface of the concavo-convex section 94*b* (particularly, a surface forming a stepped surface with respect to the longitudinal direction).

Figure 22A:
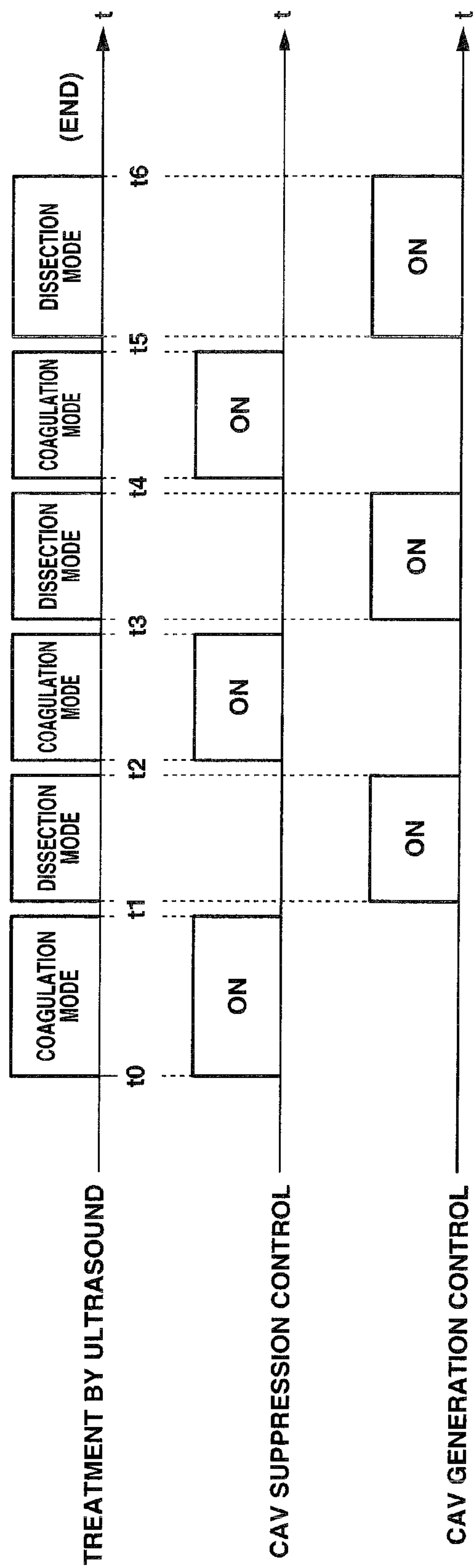
FIG. 22A and FIG. 22B are views that illustrate sequences that switch a control mode and drive in a case of performing treatment by ultrasound according to the fifth embodiment.

In the present embodiment, by employing a driving sequence as illustrated in FIG. 22A and the like as described later, coagulation/dissection treatment can be smoothly performed with respect to the living tissue 95 as the treatment target.

Figure 20C:
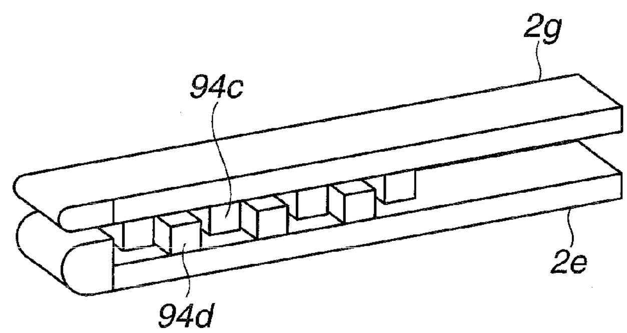
FIG. 20C to FIG. 20E are views that illustrate modification examples of the distal end section.

The shape of the distal end section in this case is not limited to the shape shown in FIG. 20A, and a structure may also be adopted that is provided with rectangular concavo-convex sections 94*c* and 94*d* as shown in FIG. 20C.

Figure 20D:
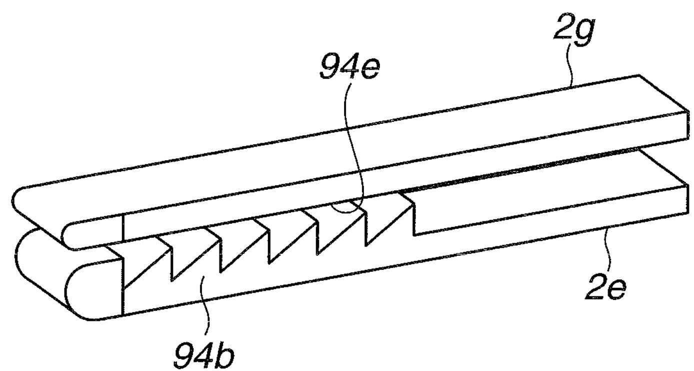
Figure 20E:
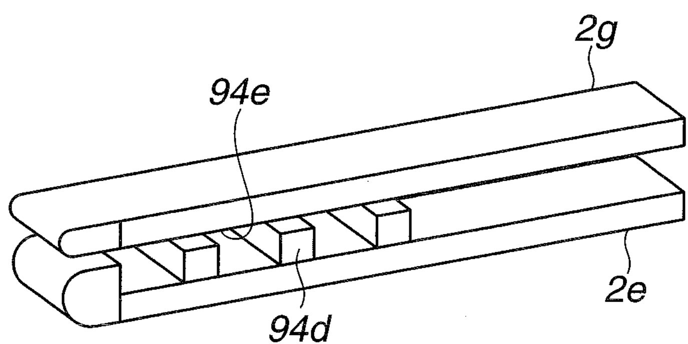

Further, as shown in FIG. 20D and FIG. 20E, a structure may be adopted in which concavo-convex sections 94*b*, 94*d* are provided only on the fixed distal end member 2*e*, and the moveable distal end member 2*g* is provided with surfaces 94*e*, 94*e* that are level or smooth with respect to the opposing surfaces of the concavo-convex sections 94*b*, 94*d*.

Figure 21:
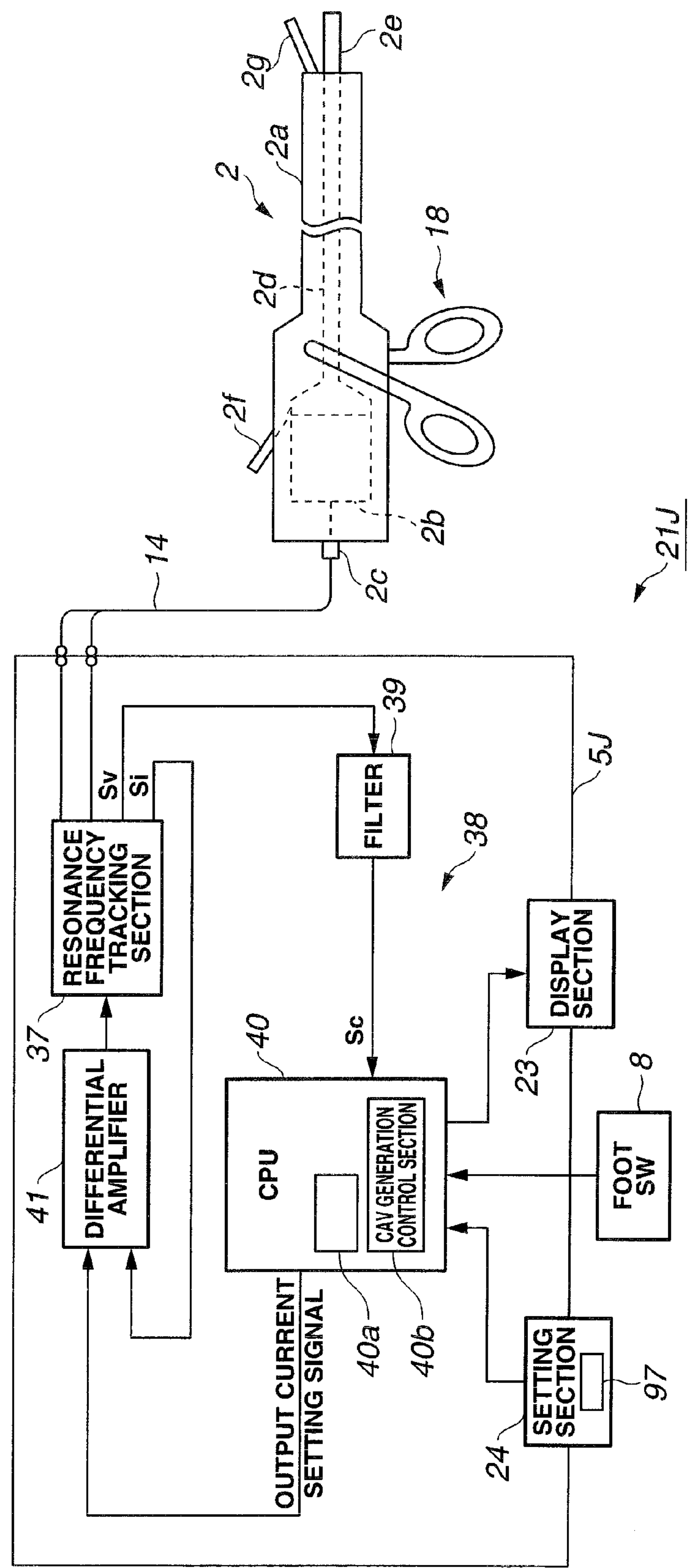
FIG. 21 is a block diagram that illustrates a configuration of an ultrasound operation apparatus according to the fifth embodiment.

FIG. 21 is a view that illustrates an ultrasound operation apparatus 21J of the present embodiment. The ultrasound operation apparatus 21J has an ultrasound driving apparatus 5J. The ultrasound driving apparatus 5J is, for example, in accordance with the ultrasound driving apparatus 5 shown in FIG. 3, and is further provided with a driving sequence setting button 97 with which the surgeon sets a driving sequence in the setting section 24.

By switching the driving sequence setting button 97 "on", the surgeon can set a time (cycle) in which to perform treatment in a tissue coagulation mode (abbreviated to "coagulation mode") that coagulates living tissue using ultrasound and a time in which to perform treatment in a tissue dissection mode (abbreviated to "dissection mode") that dissects living tissue, and can make a setting that switches between and actuates both modes.

In accordance with the setting of the driving sequence setting button 97, the CPU 40 switches output of the drive signal according to the cycle at which the coagulation mode and the dissection mode are set.

In this case, in the dissection mode the CPU 40 has a function of a cavitation generation control section (in FIG. 21, abbreviated as "CAV generation control section) 40*b* that controls so as to maintain the generation of cavitations. In contrast, in the coagulation mode, the CPU 40 controls output of the drive signal so as to enter a cavitation-free state in which cavitations are suppressed by means of the cavitation suppression control section 40*a* as described in the first embodiment and the like.

In this connection, in addition to providing the setting section 24 with the driving sequence setting button 97, a configuration may also be adopted in which, for example, a coagulation mode button and a dissection mode button are further provided to allow the surgeon to manually select the coagulation mode and the dissection mode.

The remaining configuration in the ultrasound driving apparatus 5J is the same as that of the ultrasound driving apparatus 5 shown in FIG. 3.

FIG. 22A illustrates a driving sequence in ultrasound treatment according to the present embodiment. When the treatment using ultrasound starts at, for example, a time t0, the CPU 40 sets the control mode to the coagulation mode and outputs a drive signal to the transducer 2*b* from the resonance frequency tracking section 37 constituting the drive section for a time (t1−t0) that has been set by the setting section 24.

Ultrasound vibrations generated by the transducer 2*b* are applied to the living tissue 95 from the distal end section of the probe 2*a* to perform coagulation treatment utilizing frictional heat generated by ultrasound vibrations. In this case, the CPU 40 monitors the output signal of the filter circuit 39 and controls output of ultrasound so as to suppress the generation of cavitations. That is, the CPU 40 activates the function (indicated by "ON" in FIG. 22A) of the cavitation suppression control section 40*a* when in the coagulation mode to control ultrasound output so as to enter a cavitation-free state.

When the time (t1−t0) for treatment in the coagulation mode lapses, the CPU 40 switches to the dissection mode at the time t1, and outputs the drive signal to the transducer 2*b* from the resonance frequency tracking section 37 for a time (t2−t1) that has been set by the setting section 24.

The ultrasound vibrations generated by the transducer 2*b* are applied to the living tissue 95 from the distal end section of the probe 2*a* to perform dissection treatment. In this case, the CPU 40 monitors the output signal of the filter circuit 39, and performs output control of the ultrasound so as to maintain the state in which cavitations are generated. That is, the CPU 40 utilizes cavitations to perform dissection treatment by increasing the dissection function. In FIG. 22A, CAV generation control is denoted by "ON".

When the time (t2−t1) for treatment in the dissection mode lapses, the CPU 40 switches to the coagulation mode at the time t2, and performs similar control for a time (t3−t2) that has been set by the setting section 24. The CPU 40 continues to repeat operations alternately in the coagulation mode and the dissection mode in this manner until times t4 and t5. Subsequently, upon performing treatment in the dissection mode from the time t5 to a time t6, the CPU 40 ends the coagulation/dissection treatment with respect to the living tissue that is the treatment target.

Figure 22B:
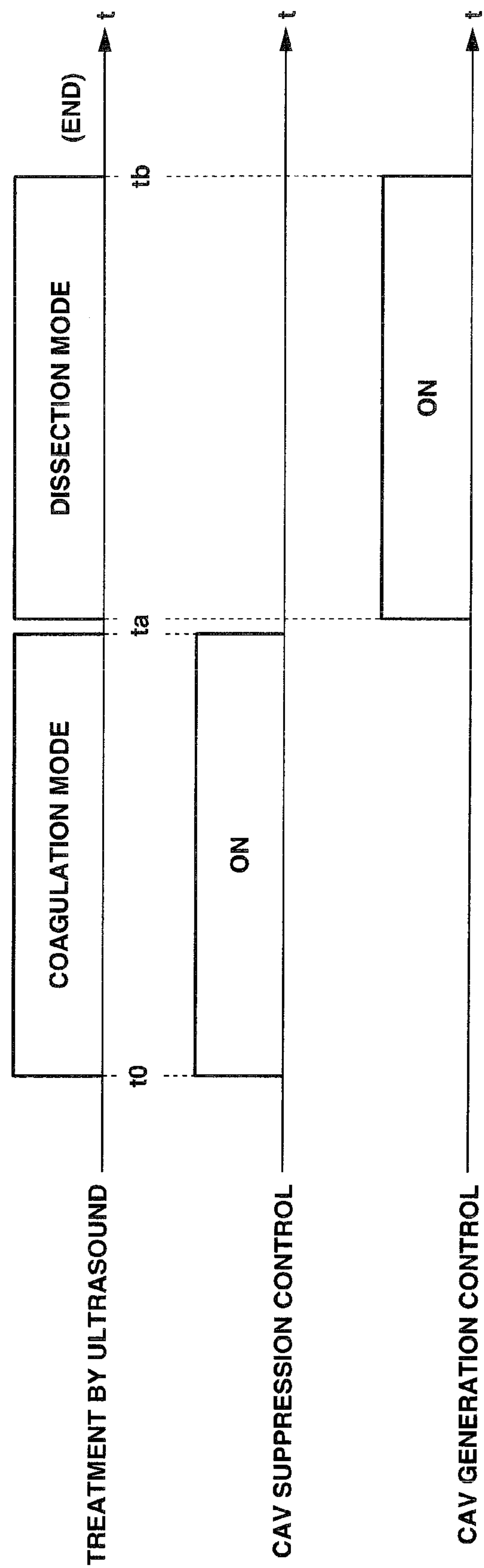

Although an example in which the coagulation mode and the dissection mode are switched and performed a plurality of times is described using FIG. 22A, as shown in FIG. 22B, a configuration may also be adopted in which the times for performing the coagulation mode and the dissection mode are lengthened to a time from t0 to ta and a time from ta to tb, respectively, so as to, for example, perform coagulation/dissection treatment with respect to the living tissue 95 that is the treatment target one time each in both modes. Furthermore, the present invention is not limited to the examples shown in FIG. 22A and FIG. 22B, and a configuration may also be adopted so as to perform treatment using a driving sequence that represents an intermediate sequence with respect to the driving sequences shown in FIG. 22A and FIG. 22B.

According to the present embodiment, coagulation treatment can be performed by suppressing the generation of cavitations in the coagulation mode. Further, in the dissection mode, treatment can be performed by generating cavitations to increase the dissection function.

Therefore, according to the present embodiment it is possible to enhance the ease of operation when a surgeon performs coagulation/dissection treatment.

In this connection, in the case of the dissection mode, a configuration may also be adopted so as to perform output control using the constant current control mode.

Having described the preferred embodiments of the invention referring to the accompanying drawings. It should be understood that the present invention is not limited to those precise embodiments and various changes and modifications thereof could be made by one skilled in the art without departing from the spirit or scope of the invention as defined in the appended claims.

What is claimed is:

1. An ultrasound operation apparatus for treating a living tissue, comprising:

an ultrasound transducer configured to generate ultrasound vibrations;

a probe having a proximal end section that is operationally coupled with the ultrasound transducer, and a distal end section configured to emit the ultrasound vibrations, the probe being configured to transmit the ultrasound vibrations generated by the ultrasound transducer from the proximal end section to the distal end section;

a resonance frequency tracking section configured to adjust a frequency of a drive signal to track a resonance frequency of the ultrasound transducer to cause the distal end section to emit ultrasound vibrations at the resonance frequency;

a setting section configured to set a setting value at a cavitation level;

a detection section configured to detect a signal level of a frequency component signal obtained by integration of the drive signal in a predetermined frequency band excluding the resonance frequency based on the drive signal adjusted by the resonance frequency tracking section; and a control section configured to control an output of the drive signal to suppress or eliminate a cavitation, based on the setting value in accordance with the signal level of the frequency component signal.

2. The ultrasound operation apparatus according to claim 1, wherein the detection section detects the signal level based on at least one of a voltage value, a current value, and an impedance value of the drive signal.

3. The ultrasound operation apparatus according to claim 1, wherein the predetermined frequency band is greater than the resonance frequency and smaller than a second-order harmonic wave of the resonance frequency.

4. The ultrasound operation apparatus according to claim 1, wherein the predetermined frequency band is at least one of a frequency band from 5% to 95% of the resonance frequency and a frequency band from 105% to 195% of the resonance frequency.

5. The ultrasound operation apparatus according to claim 1, comprising a notification section configured to provide a notification of the signal level of the frequency component signal detected by the detection section.

6. The ultrasound operation apparatus according to claim 1, wherein the control section decreases the drive signal upon detecting that the signal level of the frequency component signal has reached a first predetermined level, and increases the drive signal to a predetermined level that is lower than the first predetermined level upon detecting that the signal level of the frequency component signal has decreased to a second predetermined level that is lower than the first predetermined level.

7. The ultrasound operation apparatus according to claim 1, wherein the control section decreases the drive signal to a first predetermined level when the detection section detects that a cavitation is generated, and after one of a predetermined time elapses, or cessation of the generation of the cavitation is detected by the detection section, the control section increases the drive signal to a second level that is lower than a level at which the generation of the cavitation has been detected.

8. The ultrasound operation apparatus according to claim 7, wherein the first predetermined level is a level that is less than a boundary value at which the cavitation is generated or eliminated.

9. The ultrasound operation apparatus according to claim 1, wherein the control section switches between a plurality of control modes in which control contents are different.

10. The ultrasound operation apparatus according to claim 9, wherein the control section further comprises a setting section configured to selectively set one control mode among the plurality of control modes.

11. The ultrasound operation apparatus according to claim 9, wherein the control section identifies one or more of a type of the probe, the ultrasound transducer, or a shape or a state of use of the distal end section, and switches the control mode in accordance with a result of the identification.

12. The ultrasound operation apparatus according to claim 9, wherein the distal end section has a concavo-convex shape, and the control section selectively switches between, as the control modes, a tissue dissection mode that performs a dissection operation utilizing cavitations generated by the concavo-convex shape, and a tissue coagulation mode that performs a coagulation operation utilizing frictional heat produced by ultrasound vibrations in a condition in which cavitations are suppressed.

13. The ultrasound operation apparatus according to claim 1, wherein the control section suppresses or eliminates the cavitation by decreasing an output level of the drive signal as the signal level of the frequency component signal increases.

14. An ultrasound operation system for treating a living tissue, comprising:

an ultrasound transducer configured to generate ultrasound vibrations;

a probe having a proximal end section operationally coupled with the ultrasound transducer, and a distal end section configured to emit ultrasound vibrations, the probe being configured to transmit the ultrasound vibrations that are generated by the ultrasound transducer from the proximal end section to the distal end section;

a resonance frequency tracking section configured to automatically adjust a frequency of a drive signal to track a resonance frequency of the ultrasound transducer to cause the distal end section to emit ultrasound vibrations at the resonance frequency;

a detection section configured to detect a signal level of a frequency component signal obtained by integration of the drive signal in a predetermined frequency band excluding the resonance frequency based on the drive signal adjusted by the resonance frequency tracking section;

a suction driving section configured to suck a fluid around the distal end section;

a setting section configured to set a setting value at a cavitation level and a suction amount;

a suction control section that controls the suction driving section in accordance with the setting value set by the setting section; and a control section configured to control the vibrations of the ultrasound transducer to suppress or eliminate a cavitation in accordance with the signal level of the frequency component signal and the suction amount.

15. A cavitation suppression method for treating a living tissue, comprising:

a step of setting a setting value at a cavitation level;

a step of generating ultrasound vibrations by an ultrasound transducer;

a step of transmitting the ultrasound vibrations generated by the ultrasound transducer to a distal end section of a probe that has a proximal end section operationally coupled with the ultrasound transducer, and the distal end section that emits ultrasound vibrations;

a step of automatically adjusting a frequency of a drive signal to track a resonance frequency of the ultrasound transducer to cause the distal end section to emit ultrasound vibrations at the resonance frequency;

a step of integrating the drive signal in a predetermined frequency band excluding the resonance frequency;

a step of detecting, as a signal level of the frequency component signal, a signal obtained by integration of the drive signal, by a detection section, the signal level corresponding to a generation level of a cavitation; and a step of controlling the vibrations of the ultrasound transducer by a control section to suppress or eliminate the cavitation in accordance with the signal level of the frequency component signal.

16. The cavitation suppression method according to claim 15, wherein the control section decreases the drive signal to a predetermined level for a predetermined time when it is detected in the step of detection by the detection section that a cavitation is generated, and after the predetermined time elapses, increases the drive signal to a predetermined level that is decided in accordance with the drive signal at a time when the cavitation is generated.

17. The cavitation suppression method according to claim 15, wherein the control section decreases the drive signal when it is detected in the step of detection by the detection section that the cavitation has reached a first predetermined level, and when it is detected that the cavitation has decreased to a second predetermined level, the control section increases the drive signal to a predetermined level.

18. The ultrasound operation apparatus according to claim 1, wherein the detection section comprises a filter section that extracts a signal in a predetermined frequency band excluding the resonance frequency of the drive signal, and the detection section detects the signal level of the frequency component signal based on the signal extracted by the filter section.

19. The ultrasound operation apparatus according to claim 1, wherein the predetermined frequency band includes a frequency of a divisor of the resonance frequency.

* * * * *